(12) United States Patent
Schultz et al.

(10) Patent No.: US 7,797,988 B2
(45) Date of Patent: Sep. 21, 2010

(54) LIQUID CHROMATOGRAPHY-MASS SPECTROMETRY

(75) Inventors: Gary A. Schultz, Ithaca, NY (US); Reinaldo Rodrigo Queiros de Almeida, Arnsberg (DE); Mark Haydn Allen, East Carleton (GB)

(73) Assignee: Advion BioSystems, Inc., Ithaca, NY (US)

( * ) Notice: Subject to any disclaimer, the term of this patent is extended or adjusted under 35 U.S.C. 154(b) by 397 days.

(21) Appl. No.: 12/053,051

(22) Filed: Mar. 21, 2008

(65) Prior Publication Data

US 2008/0314129 A1  Dec. 25, 2008

Related U.S. Application Data

(60) Provisional application No. 60/896,692, filed on Mar. 23, 2007.

(51) Int. Cl.
*G01N 30/84* (2006.01)
(52) U.S. Cl. ....................................... 73/61.55
(58) Field of Classification Search ................. 73/61.55
See application file for complete search history.

(56) References Cited

U.S. PATENT DOCUMENTS

| | | | |
|---|---|---|---|
| 4,670,404 A | 6/1987 | Swift et al. | |
| 5,387,397 A | 2/1995 | Strauss et al. | |
| 5,614,154 A | 3/1997 | Glatz et al. | |
| 5,808,020 A | 9/1998 | Ferrieri et al. | |
| 5,842,787 A | 12/1998 | Kopf-Sill et al. | |
| 5,856,671 A | 1/1999 | Henion et al. | |
| 5,858,187 A | 1/1999 | Ramsey et al. | |
| 5,859,070 A | 1/1999 | Jackson et al. | |
| 5,921,678 A | 7/1999 | Desai et al. | |
| 5,922,591 A | 7/1999 | Anderson et al. | |
| 5,961,932 A | 10/1999 | Ghosh et al. | |
| 5,965,092 A | 10/1999 | Chatterjee et al. | |

(Continued)

FOREIGN PATENT DOCUMENTS

DE 102005025499 12/2006

(Continued)

OTHER PUBLICATIONS

Dewitt, "Microreactors for chemical synthesis," Current Opinion in Chemical Biology, 1999, 3:350-356.

(Continued)

*Primary Examiner*—Hezron Williams
*Assistant Examiner*—Rodney T Frank
(74) *Attorney, Agent, or Firm*—Fish & Richardson P.C.

(57) ABSTRACT

A liquid chromatography/mass spectrometry system includes a chromatographic column through which an effluent passes, wherein the effluent comprises a plurality of analytes that correspond to a plurality of chromatographic peaks and an eluent; a post-column splitter having at least two output ports through which the effluent of the column is split to at least a first portion and a second portion; a mass spectrometer configured to receive the first portion from a first of the output ports for analysis; and a tube connected to a second of the output ports configured to prevent substantial evaporation of the eluent in the second portion until undergoing mass spectrometry. The second portion has a plurality of separated analytes corresponding to at least two chromatographic peaks. A method of using the system is also disclosed.

58 Claims, 19 Drawing Sheets

U.S. PATENT DOCUMENTS

| | | | |
|---|---|---|---|
| 5,976,472 A | 11/1999 | Chatterjee et al. | |
| 6,001,229 A | 12/1999 | Ramsey | |
| 6,010,607 A | 1/2000 | Ramsey | |
| 6,033,546 A | 3/2000 | Ramsey | |
| 6,036,927 A | 3/2000 | Chatterjee et al. | |
| 6,062,261 A | 5/2000 | Jacobson et al. | |
| 6,106,710 A | 8/2000 | Fischer et al. | 210/198.2 |
| 6,110,343 A | 8/2000 | Ramsey et al. | |
| 6,117,396 A | 9/2000 | Demers | |
| 6,120,666 A | 9/2000 | Jacobson et al. | |
| 6,139,734 A | 10/2000 | Settlage et al. | 210/198.2 |
| 6,180,372 B1 | 1/2001 | Franzen | |
| 6,187,206 B1 | 2/2001 | Bernier et al. | |
| 6,231,737 B1 | 5/2001 | Ramsey et al. | |
| 6,235,471 B1 | 5/2001 | Knapp et al. | |
| 6,241,953 B1 | 6/2001 | Krijgsman | |
| 6,284,525 B1 | 9/2001 | Mathies et al. | |
| 6,315,905 B1 | 11/2001 | Settlage et al. | 210/656 |
| 6,319,476 B1 | 11/2001 | Victor, Jr. et al. | |
| 6,342,142 B1 | 1/2002 | Ramsey | |
| 6,376,181 B2 | 4/2002 | Ramsey et al. | |
| 6,409,072 B1 | 6/2002 | Breuer et al. | |
| 6,440,669 B1 | 8/2002 | Bass et al. | |
| 6,444,461 B1 | 9/2002 | Knapp et al. | |
| 6,475,363 B1 | 11/2002 | Ramsey | |
| 6,485,692 B1 | 11/2002 | Freitag et al. | |
| 6,524,456 B1 | 2/2003 | Ramsey et al. | |
| 6,537,506 B1 | 3/2003 | Schwalbe et al. | |
| 6,541,274 B2 | 4/2003 | Nagle et al. | |
| 6,572,830 B1 | 6/2003 | Burdon et al. | |
| 6,620,386 B1 | 9/2003 | Welch | |
| 6,632,656 B1 | 10/2003 | Thomas et al. | |
| 6,706,538 B1 | 3/2004 | Karg et al. | |
| 6,749,814 B1 | 6/2004 | Bergh et al. | |
| 6,794,148 B2* | 9/2004 | Jindal et al. | 435/7.1 |
| 6,806,087 B2 | 10/2004 | Kibby et al. | |
| 6,818,189 B1 | 11/2004 | Adris et al. | |
| 6,828,143 B1 | 12/2004 | Bard | |
| 6,858,435 B2 | 2/2005 | Chervet et al. | 436/161 |
| 6,890,493 B1 | 5/2005 | Bergh et al. | |
| 6,896,855 B1 | 5/2005 | Kohler et al. | |
| 6,926,313 B1 | 8/2005 | Renzi | |
| 6,958,122 B1 | 10/2005 | Gidner et al. | |
| 6,977,064 B1 | 12/2005 | Adris et al. | |
| 7,182,371 B1 | 2/2007 | Renzi | |
| 7,244,961 B2 | 7/2007 | Jovanovich et al. | |
| 2004/0022696 A1 | 2/2004 | Zigler et al. | |
| 2004/0208794 A1 | 10/2004 | Karg et al. | |
| 2004/0258615 A1 | 12/2004 | Buchanan et al. | |
| 2005/0019213 A1 | 1/2005 | Kechagia et al. | |
| 2005/0052509 A1 | 3/2005 | Gilligan et al. | |
| 2005/0181519 A1 | 8/2005 | Karg et al. | |
| 2005/0221373 A1 | 10/2005 | Enzelberger et al. | |
| 2005/0226776 A1 | 10/2005 | Brady et al. | |
| 2005/0232387 A1 | 10/2005 | Padgett et al. | |
| 2005/0252840 A1* | 11/2005 | Arnold et al. | 210/198.2 |
| 2006/0150385 A1 | 7/2006 | Gilligan et al. | |
| 2006/0289737 A1 | 12/2006 | Bassmann et al. | 250/282 |
| 2007/0071664 A1 | 3/2007 | Bellos et al. | |

FOREIGN PATENT DOCUMENTS

| | | |
|---|---|---|
| JP | 9-263591 | 10/1997 |
| JP | 2000-249694 | 9/2000 |
| JP | 2005-065632 | 3/2005 |
| PL | 0264094 | 9/1988 |
| WO | WO 99/67656 | 12/1999 |
| WO | WO 01/34660 | 5/2001 |
| WO | WO 02/11880 | 2/2002 |
| WO | WO 03/002157 | 1/2003 |
| WO | WO 03/002489 | 1/2003 |
| WO | WO 03/078358 | 9/2003 |
| WO | WO 2005/056872 | 6/2005 |
| WO | WO 2005/082535 | 9/2005 |

OTHER PUBLICATIONS

Gillies et al., J. Label. Compds. Radiopharm., 42, (1999) S886-S888.

Hadd et al., "Microchip Device for Performing Enzyme Assays," Anal. Chem. 1997, 67, 3407-3412.

Haswell et al., "Chemical and Biochemical Microreactors," The Royal Society of Chemistry 2001, Chem. Comm. 2001, 391-398.

Haswell et al., "The Application of Micro Reactors to Synthetic Chemistry," Chemical Communications, 2001, 391-398.

Jensen, "The Impact of MEMS on the Chemical and Pharmaceutical Industries," Solid-State Sensor and Actuator Workshop, So. Carolina, Jun. 4-8, 2000, 105-110.

Ramsey, "Chemistry and Chemical Analysis on Microfabricated Devices," Chemical and Analytical Sciences Division, Jan. 28, 2004, Oak Ridge, TN.

Thayer, "Harnessing Microreactions," Chemical and Engineering News, vol. 83, No. 22, May 30, 2005, 43-52.

Advion, Triversa for Metabolite Identification, (2 pages).

Amin et al., "Peak Parking Technique for the Simultaneous Determination of Anions and Cations", Anal Bioanal Chem. 381:1426-1431, 2005.

Bodnar et al., "Exploiting the Complementary Nature of LC/MALDI/MS/MS and LC/ESI/MS/MS for Increased Proteome Coverage", J Am Soc Mass Spectrom 14:971-979, 2003.

Davis et al., "Low Flow High-Performance Liquid Chromatography Solvent Delivery System Designed for Tandem Capillary Liquid Chromatography-Mass Spectrometry", J Am Soc Mass Spectrom 6:571-577, 1995.

Davis et al., "Variable Flow Liquid Chromatography-Tandem Mass Spectrometry and the Comprehensive Analysis of Complex Protein Digest Mixtures", J Am Soc Mass Spectrom 8:1059-1069, 1997.

Dionex, Probot Microfraction Collector, (4 pages).

Eksigent, "The Eksigent NanoLC System for Proteomics", www.eksigent.com, (5 pages).

Geromanos et al., "Tuning of an Electrospray Ionization Source for Maximum Peptide-Ion Transmission into a Mass Spectrometer", Anal. Chem. 72:777-790, 2000.

Goodlett et al., "Proteomics Without Polyacrylamide: Qualitative and Quantitative Uses of Tandem Mass Spectrometry in Proteome Analysis", Funct Integr Genomics 2:138-153, 2002.

Kammerer et al., "Achiral-chiral LC/LC—MS/MS Coupling for Determination of Chiral Discrimination Effects in Phenprocoumon Metabolism", Anal. Biochem. 339:297-309, 2005.

LC Packings, From the Leaders in Capillary LC, "LC/MS Tools", www.lcpakings.com, (16 pages).

Lin et al., "Peak Parking Using a Finnigan™ LCQ™ Deca", Thermo Electron Corporation, PSB 107, (2 pages).

Liu et al., "Enzyme Conformational Dynamics During Catalysis and in the 'Resting State' Monitored by Hydrogen/Deuterium Exchange Mass Spectrometry", FEBS Letters 580:5137-5142, 2006.

Lu et al., "A New Approach for Sequencing Human IRS1 Phosphotyrosine-Containing Peptides Using CapLC-Q-TOF$^{micro}$", J Mass Spectrometry 40:599-607, 2005.

Lund et al., "Comparison of Peak Parking Versus Automated Fraction Analysis of a Complex Protein Mixture", Waters, PosterREPRINT, (6 pages).

Martin et al., "Subfemtomole MS and MS/MS Peptide Sequence Analysis Using Nano-HLPC Micro-ESI Fourier Transform Ion Cyclotron Resonance Mass Spectrometry", Anal. Chem. 72:4266-4274, 2000.

Miyabe et al., "A Kinetic Parameter Concerning Mass Transfer in Silica Monolithic and Particulate Stationary Phases Measured by the Peak-Parking and Slow-Elution Methods", J. Sep. Sci. 29:2452-2462, 2006.

Okamoto et al., "On-line Sample Enrichment System Coupled to Electrospray Ionization Time-of-Flight Mass Spectrometry (ESI-TOF-MS)", J of Pharmaceutical and Biomedical Analysis 41:707-713, 2006.

Opiteck et al., "Comprehensive On-Line LC/LC/MS of Proteins", Anal. Chem. 69:1518-1524, 1997.

Pan et al., "Folding Kinetics of the S100A11 Protein Dimer Studied by Time-Resolved Electrospray Mass Spectrometry and Pulsed Hydrogen-Deuterium Exchange", Biochemistry 45:3005-3013, 2006.

Patterson et al., "Interfacing Capillary/Nano LC with MALDI/MS for High-Throughput Proteonmics", LC Packings, (1 page).

Prolexys Pharmaceuticals, Inc., "HySpec", (2 pages).

Staack et al., "The Combination of Liquid Chromatography/Tandem Mass Spectrometry and Chip-Based Infusion for Improved Screening and Characterization of Drug Metabolites", Rapid Commun. Mass Spectrom. 19:618-626, 2005.

Strittmatter et al., "Proteome Analyses Using Accurate Mass and Elution Time Peptide Tags with Capillary LC Time-of-Flight Mass Spectrometry", J Am Soc Mass Spectrom 14:980-991, 2003.

Vissers et al., "A Novel Interface for Variable Flow Nanoscale LC/MS/MS for Improved Proteome Coverage", J Am Soc Mass Spectrom 13:760-771, 2002.

Washburn et al., "Large-scale Analysis of the Yeast Proteome by Multidimensional Protein Identification Technology", Nature Biotechnology, hhtp://biotech.nature.com, 19:242-247, 2001.

Wilm et al., "Analytical Properties of the Nanoelectrospray Ion Source", Analytical Chemistry 68:1-8, 1996.

Zeller et al., "the Impact of Chromatography and Mass Spectrometry on the Analysis of Protein Phosphorylation Sites", Anal Bioannal Chem 378:898-909, 2004.

Zhou et al., "Quasi-linear Gradients for Capillary Liquid Chromatography with Mass and Tandem Mass Spectrometry", Rapid Commun. Mass Spectrom 14:432-438, 2000.

Notification of Transmittal of The International Search Report and The Written Opinion of the International Searching Authority, or the Declaration, PCT/US2008/057902, dated June 23, 2008, 12 pages.

International Preliminary Report on Patentability; PCT/US2008/057902; mailed Oct. 8, 2009.

* cited by examiner

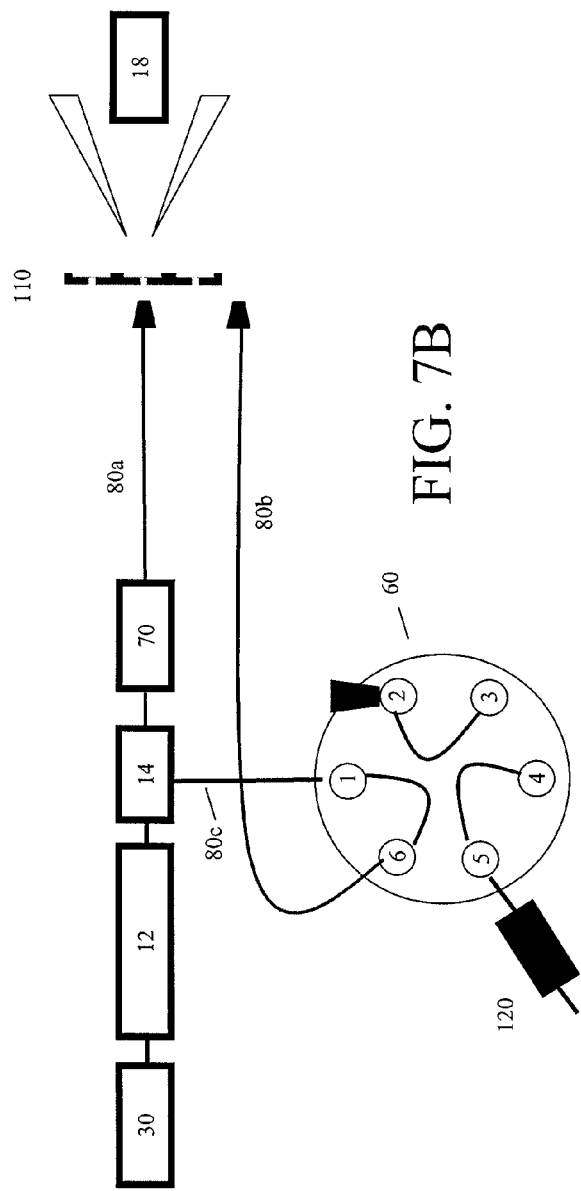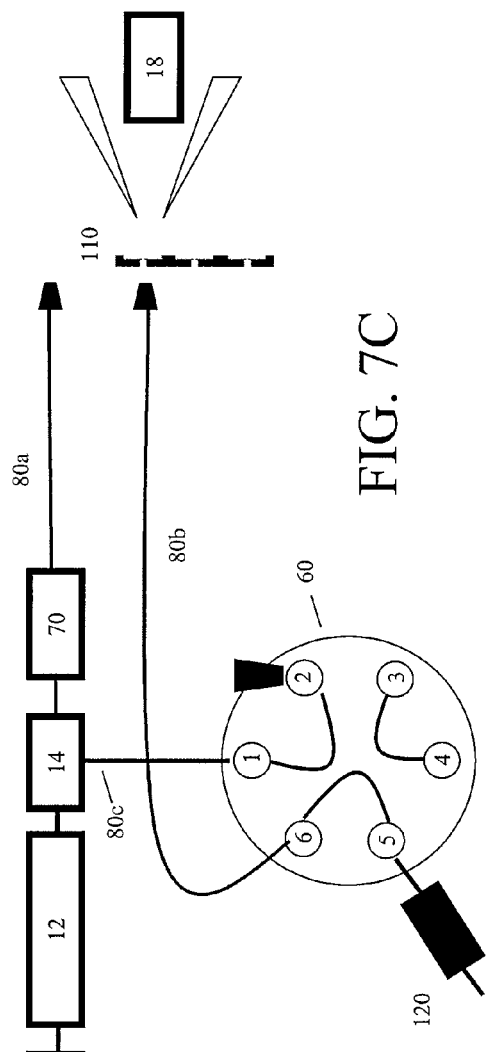

LIQUID CHROMATOGRAPHY-MASS SPECTROMETRY

CROSS-REFERENCE TO RELATED APPLICATIONS

This application claims the priority of U.S. Provisional Application Ser. 60/896,692, filed on Mar. 23, 2007, the entire content of which is incorporated by reference.

TECHNICAL FIELD

This description relates to method and system for liquid chromatography-mass spectrometry (LC/MS) analyses of biological analytes such as proteins and/or peptides, and more particularly to data dependent nano-LC/MS acquisitions.

BACKGROUND

Liquid chromatography (LC) is a well-established analytical technique for separating components of a fluidic mixture for subsequent analysis and/or identification, in which a column, microfluidic chip-based channel, or tube is packed with a stationary phase material that typically is a finely divided solid or gel such as small particles with diameter of a few microns. The small particle size provides a large surface area that can be modified with various chemistries creating a stationary phase. A liquid eluent is pumped through the liquid chromatographic column ("LC column") at a desired flow rate based on the column dimensions and particle size. This liquid eluent is sometimes referred to as the mobile phase. The sample to be analyzed is introduced (e.g., injected) in a small volume into the stream of the mobile phase prior to the LC column. The analytes in the sample are retarded by specific chemical and/or physical interactions with the stationary phase as they traverse the length of the column. The amount of retardation depends on the nature of the analyte, stationary phase and mobile phase composition. The time at which a specific analyte elutes or comes out of the end of the column is called the retention time or elution time and can be a reasonably identifying characteristic of a given analyte especially when combined with other analyzing characteristics such as the accurate mass of a given analyte. Or in other words, the analytes interact with the stationary phase based on the partition coefficients for each of the analytes. The partition coefficient is defined as the ratio of the time an analyte spends interacting with the stationary phase to the time spent interacting with the mobile phase. The longer an analyte interacts with the stationary phase, the higher the partition coefficient and the longer the analyte is retained on the LC column. An isocratic flow in LC describes a mobile phase of a constant composition. In contrast to this is the so called "gradient elution", which is a separation where the mobile phase composition changes during a separation process. For example, a 20-minute gradient starts from 10% MeOH and ends up with 30% MeOH within 20 minutes.

Detection of analytes separated on an LC or nanoLC column can be accomplished by use of a variety of different detectors. Spectroscopic detectors rely on a change in refractive index, ultraviolet and/or visible light absorption, or fluorescence after excitation with a suitable wavelength to detect the separated components. Additionally, the separated components may be passed from the liquid chromatographic column into other types of analytical instruments for further analysis, e.g., liquid chromatography-mass spectrometry (LC/MS or LC-MS) separates compounds chromatographically before they are introduced to the ion source of a mass spectrometer.

The purpose of the LC column is to separate analytes such that a unique response (e.g., a UV absorption peak) for each analyte from a chosen detector can be acquired for a quantitative or qualitative measurement. The ability of a LC column to generate a separation is determined by the dimensions of the column and the particle size supporting the stationary phase. The retention time of an analyte can be adjusted by varying the mobile phase composition and the partition coefficient for an analyte. Increases in chromatographic separation can be achieved via a reduction in the LC column diameter, increasing LC column length and/or a reduction of stationary phase particle dimensions.

Mass spectrometry ("MS" or "mass-spec") is an analytical technique used to measure the mass-to-charge ratio of gas phase ions. This is achieved by ionizing the sample and separating ions of differing masses and recording their relative abundance by measuring intensities of ion flux. A typical mass spectrometer comprises three parts: an ion source, a mass analyzer, and a detector system. The ion source is the part of the mass spectrometer that ionizes the substance under analysis (the analyte). The ions are then transported by magnetic or electric fields to the mass analyzer that separates the ions according to their mass-to-charge ratio (m/z). Many mass spectrometers use two or more mass analyzers for tandem mass spectrometry (MS/MS). The detector records the charge induced or current produced when an ion passes by or hits a surface. A mass spectrum is the result of measuring the signal produced in the detector when scanning m/z ions with a mass analyzer.

Mass spectrometry has rapidly developed as an important emerging method for the characterization of proteins. The two primary methods for ionization of whole proteins are electrospray ionization (ESI) and matrix-assisted laser desorption/ionization (MALDI). In keeping with the performance and mass range of available mass spectrometers, two approaches are used for characterizing proteins. In the first, intact proteins are ionized by either of the two techniques described above, and then introduced to a mass analyzer. In the second, proteins are enzymatically digested into smaller peptides using an agent such as trypsin or pepsin. The collection of peptide products are then introduced to the mass analyzer. The latter is often referred to as the "bottom-up" approach of protein analysis.

Proteins and/or peptides of interest to biological researchers are usually part of a very complex mixture of other proteins and molecules that co-exist in the biological medium. The high complexity of biological mixtures often makes coupling a separation technique, such as high performance liquid chromatography (HPLC), highly desirable or even required after enzymatic digestion. In addition, HPLC on-line connected to ESI-MS offers the possibility for pre-concentration of dilute samples, desalting and removal of detergents. In many applications, and especially where relatively small volumes of sample are under analysis, improving detection sensitivity can become especially important. Improvement of detection sensitivity using concentration sensitive detectors such as UV/Vis absorbance and ESI mass spectrometers can be achieved by employing HPLC columns with smaller internal diameters (i.d.). For example, increased sensitivity during peptide analysis can result from using nano-LC (e.g., column i.d. of 50-100 µm) and capillary LC (e.g., column i.d. of 320 µm). Flow rate of the mobile phase through such columns is from several nanoliters per minute (nL/min), to several microliters per minute (µL/min), and the mobile phase can be sprayed directly without post-column splitting. The process of electrospray ionization at flow rates on the order of nanoliters ("nL") per minute has been referred to as "nanoelectrospray ionization" (nanoESI).

Electrospray ionization (ESI) or nanoESI is a commonly applied ionization technique when dealing with biomolecules such as peptides and proteins. The electrospray process creates highly-charged droplets that, under evaporation, create ions representative of the species contained in the solution. An ion-sampling orifice of a mass spectrometer may be used to sample these gas phase ions for mass analysis. When an electric potential or field is applied to the outlet of a conducting needle (often referred to as a sprayer or emitter) relative to an extracting electrode, such as one provided at the ion-sampling orifice of a mass spectrometer, the electric field generated on the needle causes the separation of positively and negatively charged ions in solution and pushes ions of one polarity (e.g., positively charged or negatively charged) to the solution surface. The higher the electric field is the greater the surface charge repulsion force that counteracts the fluid surface tension is. When the repulsion force of the solvated ions exceeds the surface tension of the fluid being electrosprayed, a volume of the fluid is pulled into the shape of a cone, known as a Taylor cone, which extends from the tip of the needle. A liquid jet extends from the tip of the Taylor cone and becomes unstable and generates charged-droplets. These small charged droplets are drawn toward the extracting electrode, e.g., the sampling electrode of a mass spectrometer. The small droplets are highly-charged and solvent evaporation from the droplets results in the excess charge in the droplet residing on the analyte molecules in the electrosprayed fluid. The charged molecules or ions are drawn through the ion-sampling orifice of the mass spectrometer for mass analysis. The potential voltage ("V") required to initiate an electrospray is dependent on the size of the sprayer, the surface tension of the solution, and the electric field can be on the order of approximately $10^6$ V/m. The physical size of the needle and the fluid surface tension determines the density of electric field lines necessary to initiate electrospray.

In so-called nanoelectrospray, the sample is sprayed from a needle with a tip diameter less than about 5 μm, using a sample flow rate between 5 nL/min and 50 nL/min, for example. Charged droplets with diameters less than 1 micron can be formed at flow rates less than 40 nL/min. These small, highly-charged droplets can provide more efficient ionization of analytes contained within the droplets due to higher surface-to-volume ratios and smaller radii through which analytes need to diffuse to reach the charged surface of the droplets compared to conventional ESI. NanoESI-MS can thus be used for analyzing small amounts of sample with low sample concentrations (e.g., femtomole/microliter). Moreover, with nanoESI, the ion response for analytes contained in a sample solution is proportional to its concentration instead of its total amount. What this means is that if a solution is being sprayed at 200 nL/min or 50 nL/min or 20 nL/min the signal intensity as measured using mass spectrometry would be the same. Thus reducing a flow rate by a factor of 5 roughly increases mass spectrometry scans to be acquired for the same amount of sample by a factor of 5. As a result, signal averaging from the increased number of scans improves signal-to-noise ratios and ion statistics which enable multiple MS/MS experiments on the analytes and high accuracy in identifying analytes.

Tandem mass spectrometry (MS/MS) is a popular experimental method for identifying biomolecules such as proteins. Tandem MS involves multiple steps of mass selection or analysis, usually separated by some form of fragmentation. A tandem mass spectrometer is capable of multiple stages of mass spectrometry. For example, one mass analyzer can isolate one peptide from many others entering a mass spectrometer. A second mass analyzer then stabilizes the peptide ions while they collide with a gas, causing them to fragment by collision-induced dissociation (CID). A third mass analyzer then characterizes the fragments produced from the peptides. Tandem MS can also be done in a single mass analyzer over time as in a quadrupole ion trap. There are various methods for fragmenting molecules for tandem MS, including collision-induced dissociation (CID), electron capture dissociation (ECD), electron transfer dissociation (ETD), infrared multiphoton dissociation (IRMPD) and blackbody infrared radiative dissociation (BIRD).

Characterization of total digests (peptides) of complex protein mixtures using HPLC/MS is also called shotgun proteomics. Shotgun analysis involves direct digestion of protein mixtures to complex peptide mixtures, followed by the automated identification of the peptides by liquid chromatography combined with tandem mass spectrometry (LC-MS/MS). The development of shotgun proteomics today couples nano-LC for peptide analysis, automated MS to MS/MS data acquisition software and hardware on modern tandem mass spectrometers, along with data searching software of modern search engines. Modern mass spectrometers with data dependent scanning software are capable of acquiring MS and MS/MS data from many hundreds of peptides per hour.

The principle of shotgun analysis is to first "spread out" peptides in complex mixtures by multidimensional chromatographic separation. Tandem MS instruments then acquire peptide MS/MS spectra, which encode the peptide sequences. This acquisition can be done in a data-dependent way, whereby the instrument relies on a preliminary scan, performed as the peptides enter the instrument, to select peptides for fragmentation and generation of MS/MS spectra.

SUMMARY

In one aspect, in general, a liquid chromatography system includes: a chromatographic column through which an effluent passes, wherein the effluent comprises a plurality of analytes that correspond to a plurality of chromatographic peaks and an eluent; a post-column splitter having at least two output ports through which the effluent of the column is split to at least a first portion and a second portion; a mass spectrometer configured to receive the first portion from a first of the output ports for analysis; and a tube connected to a second of the output ports configured to prevent substantial evaporation of the eluent in the second portion until undergoing mass spectrometry. The second portion has a plurality of separated analytes corresponding to at least two chromatographic peaks.

Aspects can include one or more of the following features.

The system is configured to direct the second portion to the mass spectrometer after the first portion is analyzed by the mass spectrometer.

The system further comprises a pump connected to the tube to pump the second portion to the mass spectrometer after the first portion is analyzed by the mass spectrometer.

The system further comprises a second detector configured to receive the second portion from the tube after the first portion is analyzed by the mass spectrometer.

The second detector comprises a mass spectrometer.

The second detector comprises an infusion nanoESI/MS device.

The tube is configured to substantially reduce the diffusion of the analytes in the effluent stored in the tube.

The tube is configured to stay at a temperature lower than the room temperature.

The tube comprises an electrolysis electrode to electrolyze the eluent to produce a gas segment between any two eluent segments.

The electrolysis is triggered by an analytical device.

The device is an ultraviolet detector, fluorescence detector, an electrochemical detector, evaporative light scattering detector, nuclear magnetic resonant spectrometer, charged aerosol detector, refractive index detector, or a mass spectrometer.

The mass spectrometer comprises an electrospray sprayer.

The mass spectrometer comprises an ESI/MS device.

The mass spectrometer comprises an infusion nanoESI/MS device.

The infusion nanoESI/MS device comprises a nanoESI sprayer.

The nanoESI sprayer comprises a pulled tip of a fused silica capillary.

The infusion nanoESI/MS device comprises a chip containing an array of nanoelectrospray nozzles.

The tube comprises a fused silica capillary.

The tube has a diameter of 250 μm or less.

The tube has a diameter of 100 μm or less.

The tube has a diameter of 75 μm or less.

The tube has a diameter of 50 μm or less.

The tube has a length of about 1 meter or more.

The tube has a length of about 10 meters or less.

The tube has a length of about 6 meters.

The second portion is directed for mass spectrometry at a lower flow rate than the first portion is.

The splitter comprises a T-shape piece that creates a volume ratio of about 4:1 to about 1:1 of the second portion to the first potion.

The splitter comprises a valve that has at least five ports, a first connector connecting two of said ports, and a second connector connecting three or more of the rest said ports to split the effluent.

The valve has at least six ports.

The valve has at least one port connected to a flow controller.

The valve has two ports that are connected by the tube.

The valve is switchable between at least two configurations, including a first configuration in which the second connector connects a first set of three ports, and a second configuration in which the second connector connects a second set of ports different from the first set.

The analytes in the second portion exit the tube in the same order in which the analytes exit the chromatographic column.

The analytes in the second portion exit the tube in a reversed order in which the analytes exit the chromatographic column.

The second portion is mixed with a stream of liquid before the portion undergoes mass spectrometry.

The second portion has a plurality of separated analytes corresponding to at least half of the plurality of chromatographic peaks corresponding to the analytes that pass through the chromatographic column.

The second portion has a plurality of separated analytes corresponding to at least 90% of the plurality of chromatographic peaks corresponding to the analytes that pass through the chromatographic column.

The system further comprises a second chromatographic column, wherein the inner diameter of the second column is smaller than that of the first column.

In another aspect, in general, a method of characterizing an analyte in a sample includes: passing an effluent comprising a plurality of analytes and an eluent through a chromatographic column, the analytes corresponding to a plurality of chromatographic peaks; splitting at least a first portion and a second portion of the effluent from respective output ports of a post-column splitter, the first portion being directed from a first of the output ports to a mass spectrometer for analysis; and receiving the second portion having a plurality of separated analytes corresponding to at least two chromatographic peaks in a tube connected to a second of the output ports to prevent substantial evaporation of the eluent before undergoing mass spectrometry.

The method further comprises directing the second portion from the tube to the mass spectrometer after the first portion is analyzed by the mass spectrometer.

The method further comprises directing the second portion from the tube to a second mass spectrometer after the first portion is analyzed by the mass spectrometer.

The method further comprises analyzing a first analyte from the stored second portion after a second analyte from the first portion has been analyzed by the mass spectrometer, wherein the first analyte passed out of the chromatographic column before the second analyte passed out of the chromatographic column.

The method further comprises analyzing a first analyte from the stored second portion after a second analyte from the second stored portion has been analyzed by the mass spectrometer, wherein the first analyte passed out of the chromatographic column before the second analyte passed out of the chromatographic column.

The method further comprises analyzing a first analyte from the stored second portion before a second analyte from the second stored portion has been analyzed by the mass spectrometer, wherein the first analyte passed out of the chromatographic column before the second analyte passed out of the chromatographic column.

The method further comprises cooling the second portion to substantially reduce diffusion of the analytes in the eluent captured in the tube.

The method further comprises segmenting the stored second portion into a least two segments in the tube by a gas bubble wherein the gas bubble creates a diffusion boundary to the analytes in the portion.

The gas bubble is formed by electrolysis of the eluent of the second portion.

The method further comprises recording the segment positions in the tube by counting gas bubbles.

The method further comprises segmenting the stored second portion into at least two segments in the tube by a non-mixing liquid segment wherein the non-mixing liquid segment creates a diffusion boundary to the analytes in the portion.

The method further comprises directing the stored second portion in the tube to the mass spectrometer at a calibrated flow rate controlled by a pump connected to the tube.

The calibrated flow rate is less than 5,000 nL/min.

The calibrated flow rate is less than 1,000 nL/min.

The calibrated flow rate is less than 200 nL/min.

The second portion has a plurality of separated analytes corresponding to at least half of the plurality of chromatographic peaks corresponding to the analytes that pass through the chromatographic column.

The second portion has a plurality of separated analytes corresponding to at least 90% of the plurality of chromatographic peaks corresponding to the analytes that pass through the chromatographic column.

The method further comprises directing the effluent into a second chromatographic column.

The directing is performed by controlling back pressures of the splitter by connecting a pump to a port of the splitter.

Aspects may include one or more of the following advantages.

A post-column splitter can divide a liquid chromatographic effluent such that a first fraction of the effluent is subjected to immediate nanoelectrospray mass spectrometry analysis while a second fraction is captured and stored in a tube, e.g., a capillary tube with i.d. of about a few tens of microns. The splitter can be a T-shape piece, or chip-based channels, or a multi-port valve that can divide the effluent. The splitter can also be configured to divide the effluent to more than two fractions thus allow more than one fractions to be captured and stored in individual tubes for later usage. The dimension of the capture tube is selected to control diffusion of analytes molecules so that the degree of remixing of the separated analytes can be controlled or minimized. Gas segments can be introduced to the captured fraction to further limit diffusion of LC-separated analytes to confined regions and thus greatly increase storing time of the faction. Moreover, using a tube to store a fraction of the LC effluent allows the analyte molecules maintained in a solution, e.g., to prevent decomposition of the analyte upon drying or to prevent loss of precious sample by drying and redissolving it in a solvent. The second fraction collected in the tube can be redirected to a nanoESI sprayer to enable additional MS data to be acquired from the same sample injection based on the initial MS analysis of the first fraction, e.g., at a lower flow rate to the sprayer for targeted analytes or skipping analysis of less interesting analytes in the fraction to save time. The captured fraction can also be modified or treated before MS analysis by, e.g., adding another solvent, or undergoing another LC analysis, e.g., ion exchange chromatography.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 7A-C are schematics of embodiments with a capture capillary.

DETAILED DESCRIPTION

Figure 1A:
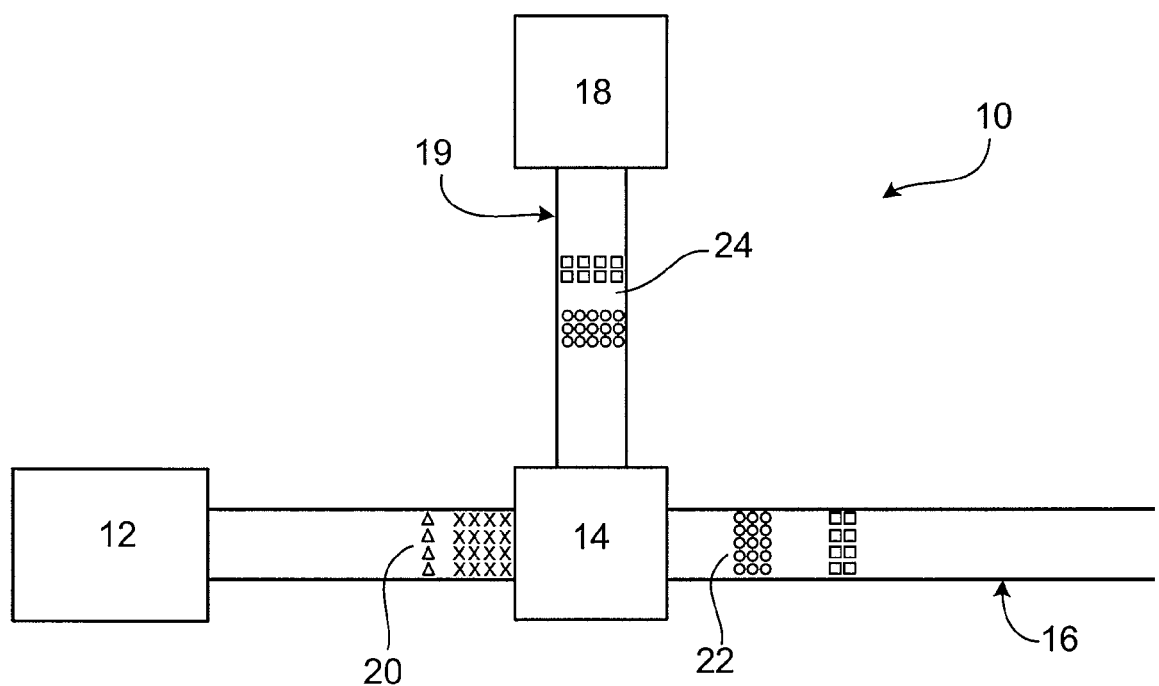
FIG. 1A is a simplified cross-sectional schematic of a LC/MS system.

Liquid chromatography (LC) with columns of small internal diameters, e.g., capillary LC and nano-LC columns, can be coupled with nanoESI to combine the benefits of sample separation and/or concentration in columns of small diameters and improved ionization efficiencies with nanoESI. For good LC separation resolution, peak widths should be narrow, but narrow peaks limit the acquisition time for mass spectral data. Preferably, an analytical system should enable separation of all compounds within an HPLC system (narrow peaks and high peak capacity), while enabling essentially unlimited time to acquire mass spectrometric data for each separated compound. For example, peak width at half height of compounds eluting from capillary- or nano-LC columns is generally in the range of 5 seconds to 30 seconds. During this period, the peptide needs to be sequenced, which may require multiple stages of MS detection. Sequencing of the peptides is performed by comparing measured and calculated fragment spectra. These scan cycles take approximately a few hundred milliseconds to a few seconds, which allows the experiment to perform only limited numbers of cycles during the elution of a chromatographic peak.

Some nano-LC/nanoESI-MS techniques spray the entire effluent exiting the nano-LC column with a nanoESI sprayer. As discussed above, each analyte eluting from a column occurs as a transient with a time profile of seconds. When samples become complex and contain multiple analytes that are co-eluting, data-dependent scanning or other methods of MS/MS such as ECD or ETD may not be able to acquire spectra fast enough to identify all the analytes, e.g., peptides, as they enter the MS instrument, thus many analyte identifications can be missed. Often times it is only possible to collect MS/MS data on components of highest intensities in the initial MS scanning, thus restricting dynamic range for component identification.

The present disclosure includes description of techniques that are able to solve these problems. For example, the strengths of nano liquid chromatography/mass spectrometery (nanoLC/MS) and infusion nanoelectrospray mass spectrometry (nanoESI/MS) can be combined with a post-column splitter that divides the LC effluent such that a first portion or fraction of the effluent is subjected to nanoelectrospray mass spectrometry analysis immediately after chromatographic separation and a second portion or fraction is captured and stored in a tube, e.g., a capillary tube with i.d. of about 20-50 µm. After a short time, e.g., following completion of the LC separation of the entire or partial sample injection, and/or completion of an initial MS analysis of the first portion of the effluent, the second portion collected in the tube can be redirected to a nanoESI sprayer to enable additional MS data to be acquired from the same sample injection based on the initial MS analysis to allow more signal averaging and improve accuracy of sample identification or proteome coverage in a shotgun experiment, for instance.

Referring to FIG. 1A, an LC/MS system 10 includes a liquid chromatographic column 12, e.g., a nano-LC column, which provides on-line separation capabilities to mass spectral analysis of the effluent 20 containing a plurality of separated analytes (illustrated as squares, circles, crosses, and triangles). A portion 24 of the effluent 20 is directed via some tubing 19 (e.g., a capillary tube) to mass spectrometer or MS device 18, e.g., a nanoESI/MS device. Another portion 22 of the effluent 20 is simultaneously captured and stored in a tube 16 which is configured to control (e.g., to reduce) the diffusion of the analytes in the effluent inside the tube 16 and substantially preserve the chromatographic separation of analytes from the column 12. The effluent 20 is split by a post-column splitter 14 to at least two portions 22 and 24. While the portion 24 is undergoing mass spectral analysis in the MS device 18, the portion 22 of the effluent can, in some cases, keep entering tube 16 and keep moving along in tube 16. Or, in other cases in which it may be desirable to store the portion 22 for longer periods of time, the portion 22 can be kept substantially stationary in tube 16 for a period of time that is long enough for the MS device 18 to further analyze the portion 24. Usually after the scanning of the portion 24 has been completed, the portion 22 can be redirected through the tube 16 and the splitter 14 to the MS device 18 (or redirected to a different MS device) for a second round of analysis, e.g., tandem MS. In some embodiments, tubing 19, splitter 14, and/or the tube 16 and can be integrated into a microfluidic chip, e.g., a chip containing a splitter connected to a long channel (e.g., a microfluidic channel) functioning as tubing 19 and/or tube 16.

In some embodiments, column 12 can be an HPLC column with an internal diameter in the micrometer scale, e.g., a nano-LC column of 75 µm i.d., and the flow rate can be controlled by a nano-LC pump to range between about 10 nL/min to 1000 nL/min, e.g., about 200 nL/min to 300 nL/min.

Figure 1B:
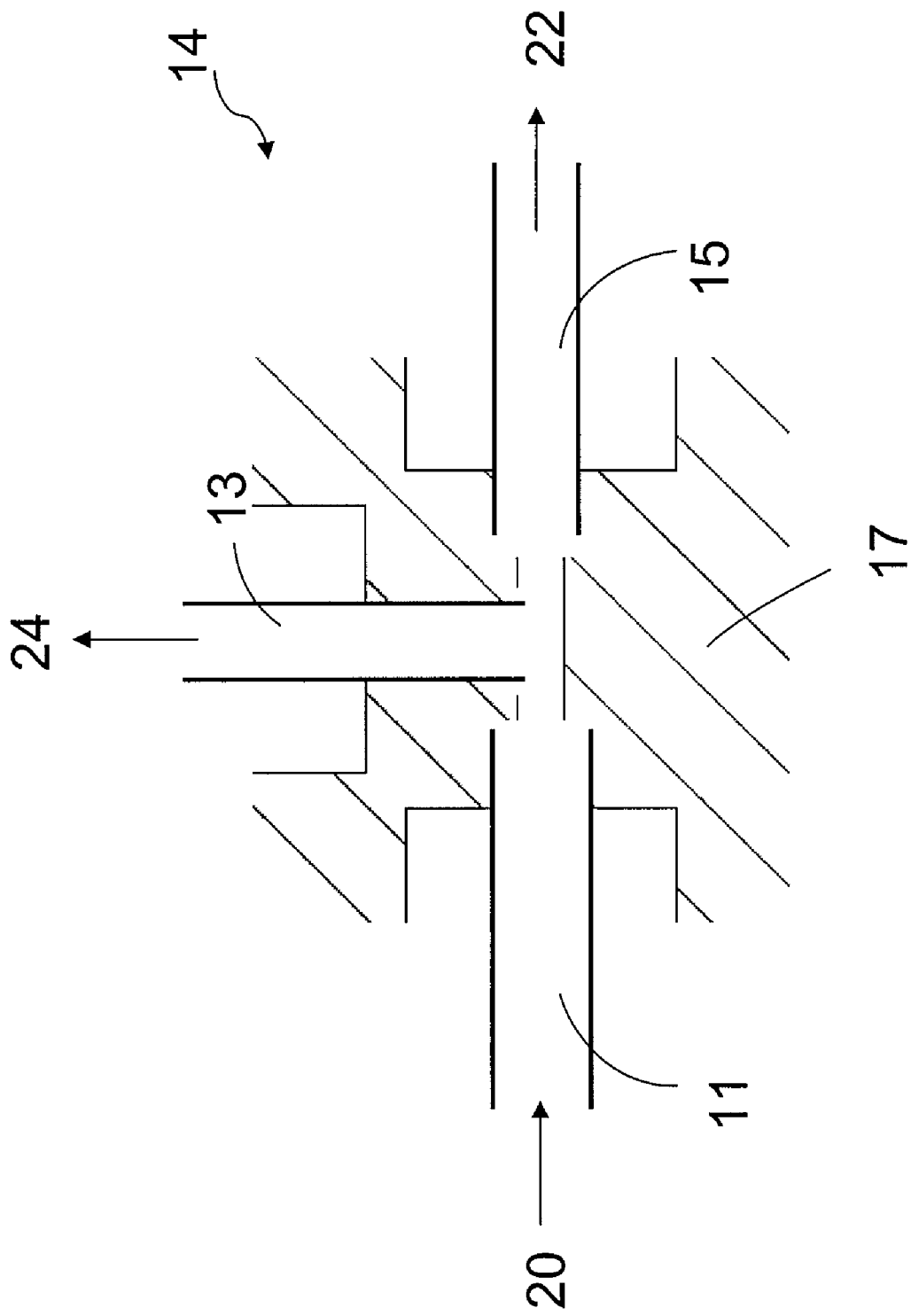
FIG. 1B is a cross-sectional schematic of an embodiment.

The post-column splitter 14 can be a T-shape piece ("Tee") as shown in FIG. 1B. Referring particularly to FIG. 1B, the T-shape piece includes an input port 11 which can be connected to an outlet of the nano-LC column, two output ports 13 and 15 which divides the LC effluent 20 entering the Tee into two portions (shown as portion 24 to MS device and portion 22 to capture tube), and an air tight fitting 17 which holds the three ports together and allows fluid communication between the ports. Each of the two output ports can be an integral part of the tubing or tube that the two split portions enter respectively, e.g., port 13 can be the proximal end of tubing 19 (in FIG. 1A) and port 15 can be the proximal end of tube 16 (in FIG. 1A) with respect to the flow direction. The split ratio, usually the flow rate ratio of the two portions 24 and 22, e.g., portion to be analyzed vs. portion to be stored, can be adjustable from 1:100 to 10:1, e.g., from 1:10 to 5:1, from 1:3 to 4:1, from 1:1 to 3:1, according to different experimental needs. For example, if flow rate of portion 24 is required to be 50-100 nL/min, when the flow rate of the LC effluent is 200 nL/min, the flow rate ratio would be selected to be 1:3 to 1:1.

The flow rate ratio can be adjusted by controlling the back pressures of the output ports of the splitter. There are several factors that influence back pressure, such as the inner diameters and lengths of the output ports and tubes connected to them. In some embodiments, the inner diameters of the output ports and/or the tubes connected to them can be about 5 µm to 750 µm, e.g., 10 to 500 µm, 20 to 200 µm, or 50 to 100 µm. For example, in a particular embodiment, port 13 can have 15 µm i.d. with 15 centimeters of total tubing length while port 15 has 50 µm i.d. with 600 cm of total tube length to achieve a flow rate ratio of 1:3. Back pressure can also be affected by applying external pressure to the split portions via, e.g., a spit adjustor, more detail of which follows.

Figure 2A:
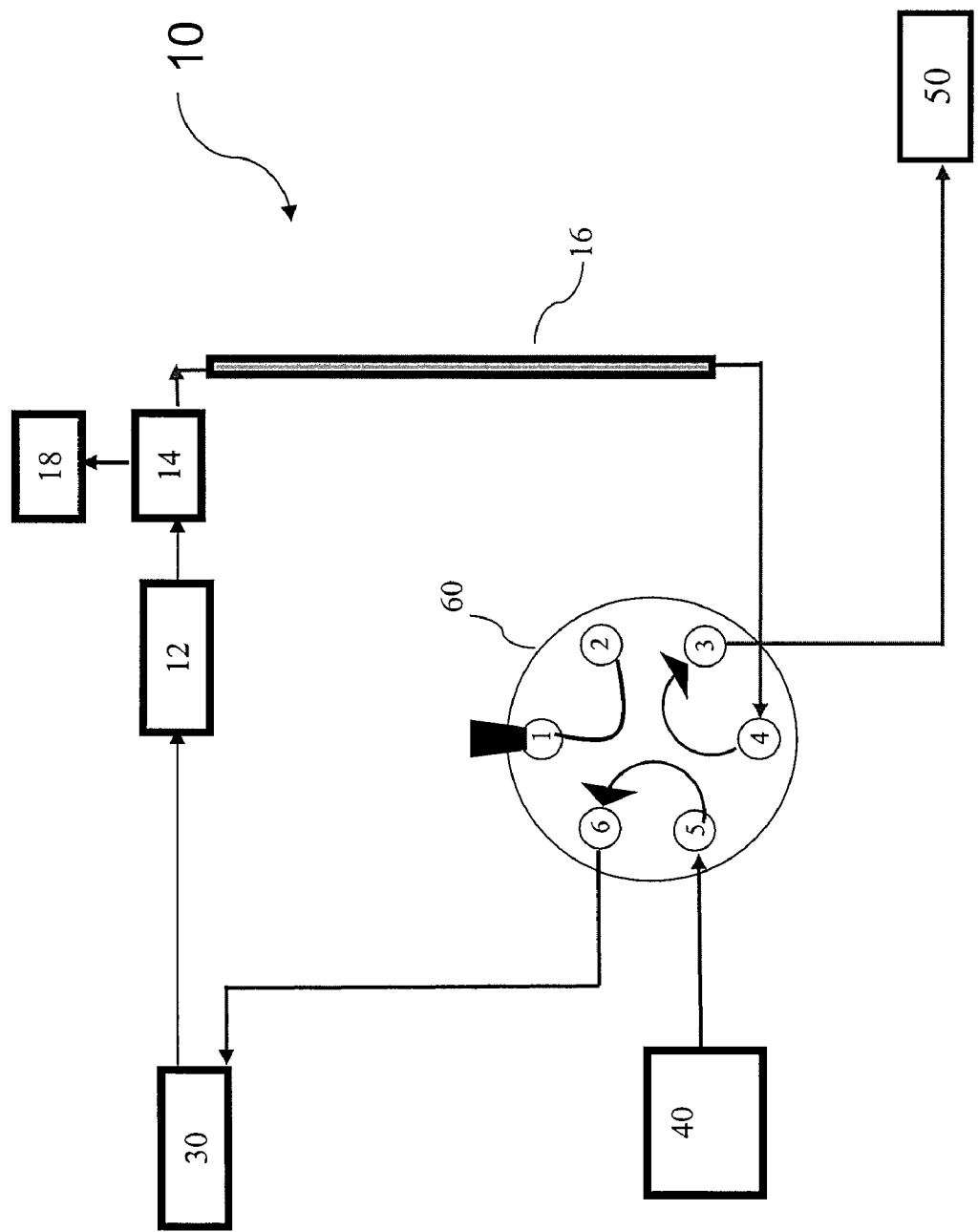
FIGS. 2A and 2B are schematics of a LC/MS system.
Figure 2B:
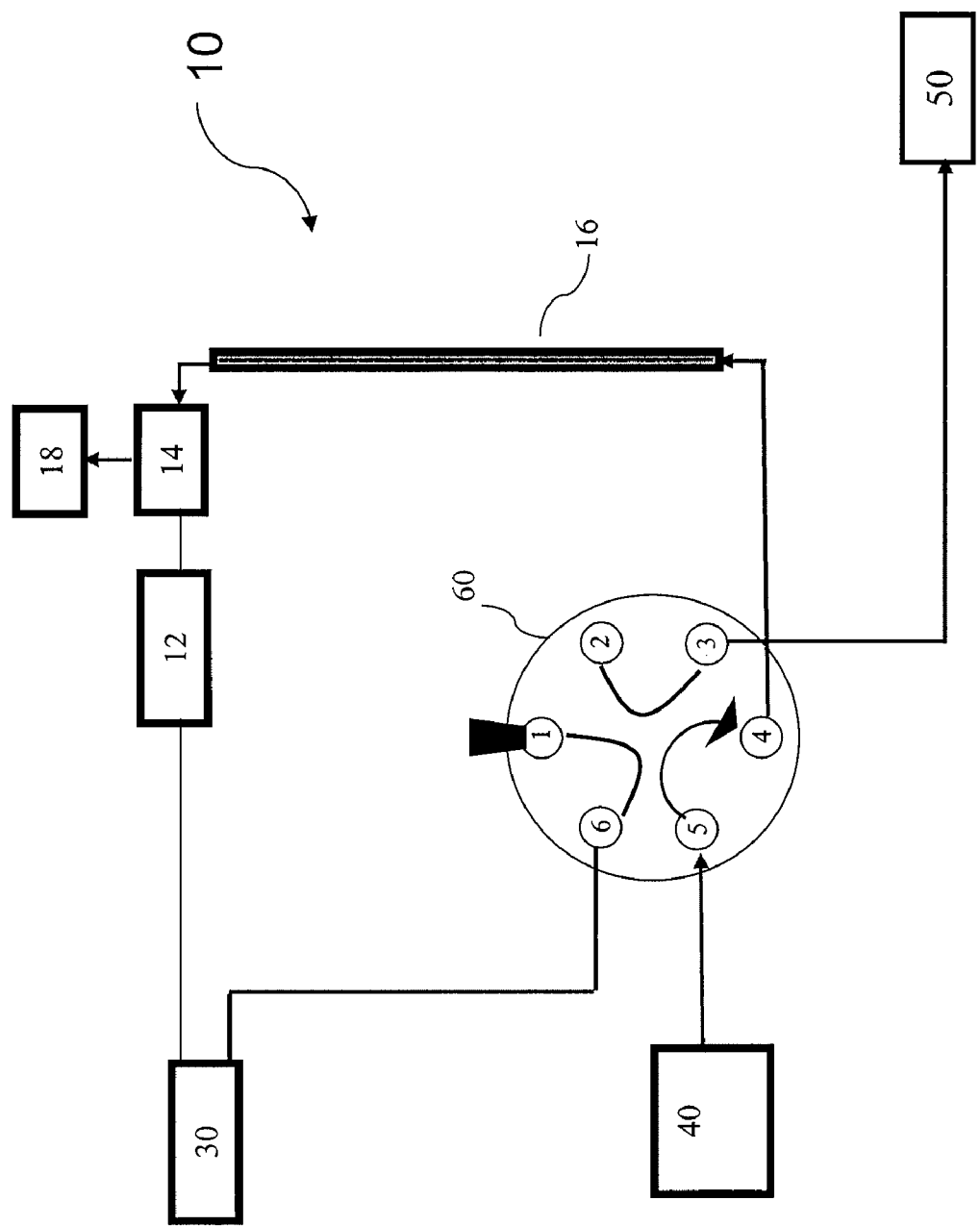

Referring particularly to FIGS. 2A and 2B, an LC/MS system 10 can further include an autosampler 30 upstream of the LC column 12. The mobile phase or the eluent for LC is driven by a pump 40 which can also adjust the flow rate of mobile phase on the order of nL/min. The arrows in FIGS. 2A and 2B indicate flow directions of the mobile phase. The system 10 can switch between a first "online LC/MS plus splitting" mode (FIG. 2A) and a second "no-splitting infusion" mode (FIG. 2B) via use of a multiple port valve, e.g., a micro switching valve 60 having six ports labeled 1 through 6 with every port connectable to either one of the two neighboring ports through a connector such as a groove or channel (not shown but connection is illustrated by arrows or lines between each two ports) in the valve. For example, for system 10 to be in the first mode as shown in FIG. 2A, ports 5 and 6 of valve 60 are in fluid communication so that the pump 40 can drive the mobile phase to carry the sample from the autosampler through the LC column 12 then through post-column splitter 14. As discussed above, a first portion of the effluent of column 12 is directly driven to the mass spectrometer 18 while a second portion is captured by a tube 16. A device 50 is connected to port 3 of the valve 60. In some cases, the device 50 can be a waste or a split adjustor for, e.g., controlling the flow rate of the captured portion in tube 16. In other cases, the device 50 can be a second mass spectrometer, e.g., a nanoESI/MS device to analyze the captured portion based on the analysis results from the first portion.

For system 10 to be in the second mode as shown in FIG. 2B, ports 5 and 4 of valve 60 are in fluid communication so that the pump 40 can drive the captured portion of LC effluent back to the splitter 14 then to MS device 18 where the order of analytes in the captured portion entering the MS device is reversed due to this set up configuration, i.e., the first into the tube will be the last out for MS analysis. In this mode, since port 1 is blocked with a plug or the like, the back pressure of column 12 can prevent the captured portion flowing back to the LC column. In some embodiments, a closing valve might be used between column 12 and splitter 14 to prevent the backflow to column 12. The selection between the two modes can either be manually or automatically controlled. The timing of switching from one mode to another can be experiment specific. For example, one can switch system 10 from the first mode to the second only after all components of the sample has been LC separated and eluted; or one can do so intermittently by pausing the LC separation when it is necessary. In some embodiments, the captured effluent portion may be directed to another analytical device or another mass spectrometer, e.g., another nanoESI/MS.

Figure 3A:
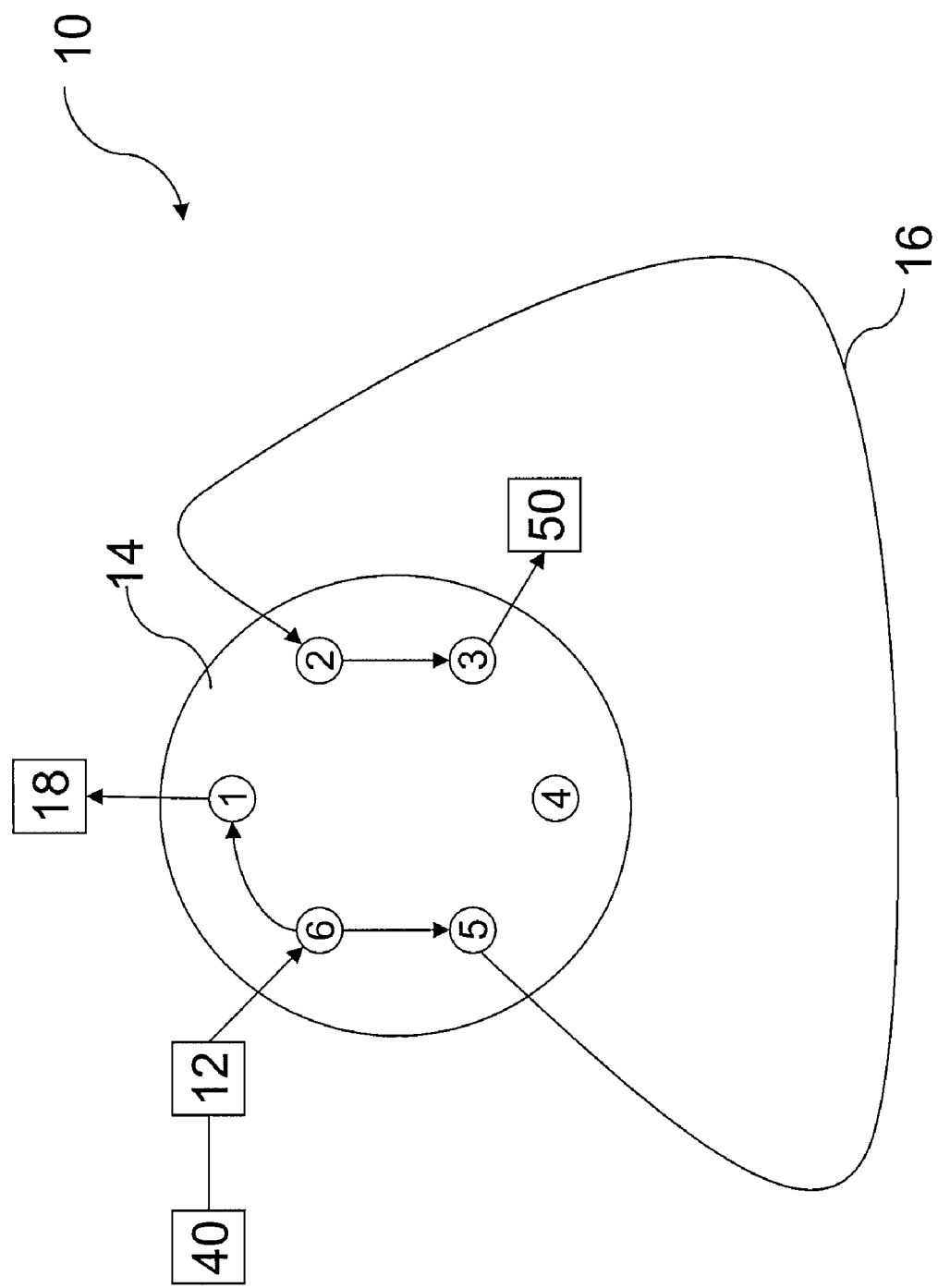
FIGS. 3A-G are schematics of another embodiment.
Figure 3B:
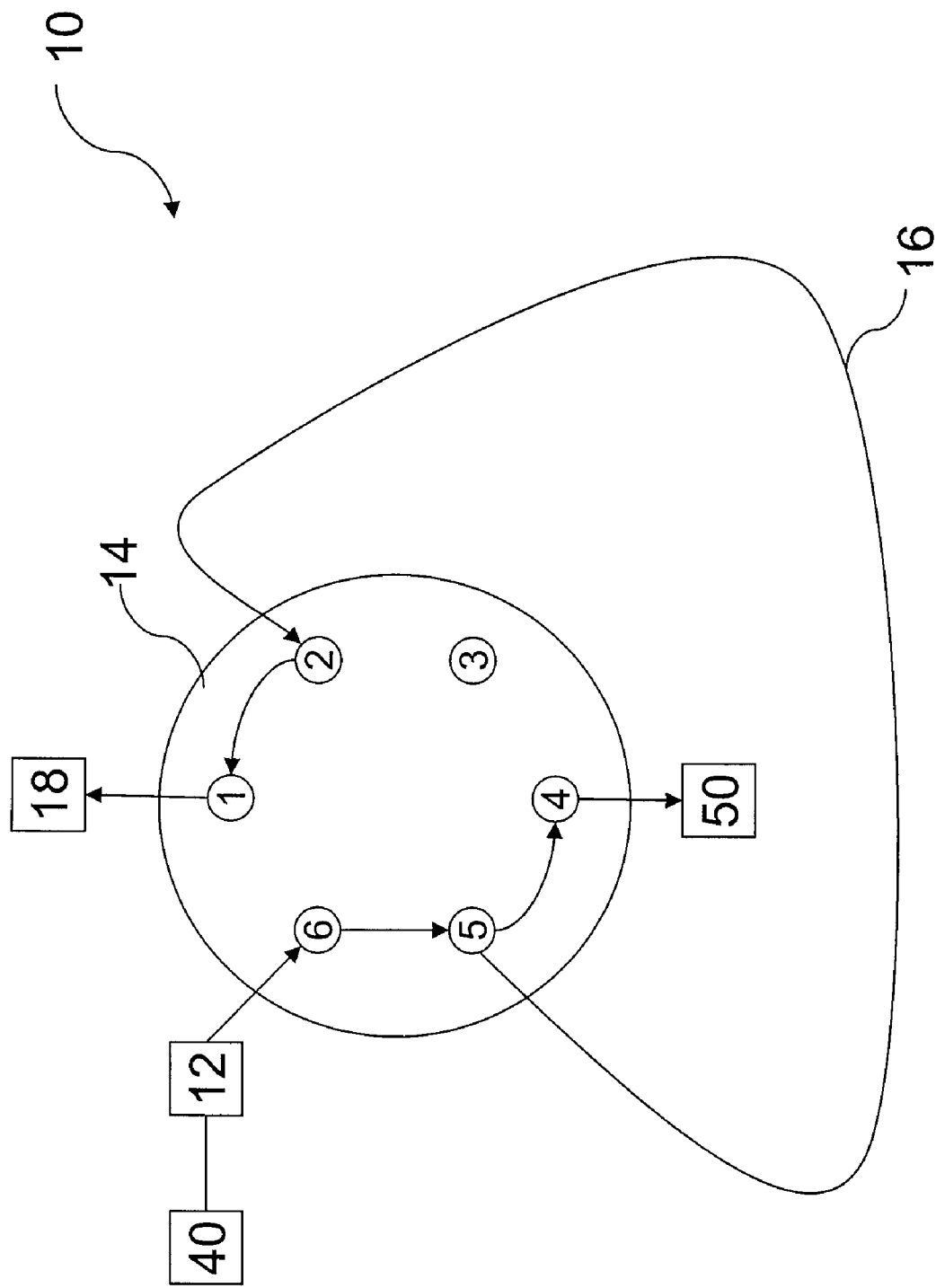

In other embodiments, splitter 14 can be a multiple-port micro switching valve with at least one groove or channel that connects three or more ports simultaneously so that the valve can not only exhibit the same function as a T-shape splitter but also have additional functional features. As an example, a 6-port valve is shown in FIGS. 3A through 3F. Arrows in these figures indicate flow directions of the analytes. Referring particularly to FIG. 3A, valve 14 is in the 'splitting and capture' mode, and unlike in a conventional switching valve, port 6 is connected to both of its two neighboring ports (ports 1 and 5) through a groove or channel of the valve as well as connected to an outlet of the LC column 12 simultaneously so that the effluent from column 12 can be split into two portions with one flowing to the MS device 18 while the other flowing into a capture tube 16 connecting ports 5 and 2. Ports 2 and 3 are connected through another groove or channel of the valve in this mode. Port 3 is also connected to a split adjuster 50 to adjust the nanoLC split ratio, e.g., the flow rate ratio of port 1 to port 5, while port 4 is isolated from the other ports. The split adjuster can either be a pressurized vessel or a pump, which is used to adjust the back pressure of the tube 16 in order to control the split ratio, as discussed above. Referring particularly to FIG. 3B, valve 14 is switched to the 'infusion' mode. The groove that connected port 6 to ports 1 and 5 in the 'splitting and capture' mode now rotates counterclockwise so that port 5 is connected to both of its neighboring ports (ports 4 and 6) simultaneously while the groove that connected ports 2 and 3 now connects ports 1 and 2. The resulting configuration is then port 6 connected to the pump 40 through column 12 and port 2 connected to port 1 so that the captured portion of separated analytes in tube 16 between ports 5 and 2 can be driven by the mobile phase of column 12 into the MS device 18 through port 1. The flow rate of the mobile phase is controlled by pump 40. Optionally, port 4 can connect to a split adjuster 50 to adjust the flow rate of the captured portion entering MS device 18 without having to decrease the flow rate of the mobile phase in LC column 12. For example, the flow rate in LC column can be kept at 200 nL/min while the flow rate in tube 16 can be adjusted to 50 nL/min by bifurcating the mobile phase exiting the LC column at port 5 with about three fourths of the mobile phase flowing to port 4 with the assistance of the split adjuster 50. In some embodiments, the captured effluent portion may be directed to another analytical device or is 5 another mass spectrometer, e.g., an nanoESI/MS. In some embodiments, in this 'infusion' mode, the flow for infusion nanoESI/MS of the captured chromatogram can be driven by the column wash in the column regeneration steps thereby enabling simultaneous infusion experiment and column preparation for the next injection which leads to an improvement in speed and efficiency of the analytical process, for example. In embodiments, the grooves in the valve connecting neighboring ports have a width of about 10-150 µm and a depth of about 5-75 µm. Compared to the set up configuration with a T-shape splitter discussed above, the valve structure of splitter 14 enables the order of the analytes in the captured portion entering the MS device to be the same order of exiting the LC column, i.e., the first into the capture tube will be the first out for MS analysis. One potential benefit of using this valve configuration is that the analytes or components captured into the tube each go in one end and out the other, thereby traversing the same length and are subjected to a similar degree of diffusion so that the chromatographic peaks have similar degree of broadening.

In some embodiments, composition modification or treatment of the captured portion of the separated analytes in tube 16 may be desired, e.g., adding a different mobile phase to increase ionization of the analytes for mass spectrometry experiment. The modification of the captured portion may achieve, e.g., changes in ionization, electrochemical modification of captured components, enzyme degradation of intact proteins or peptides, mass tagging, or enzymatic de-phosphorylation of peptides or proteins, thus providing additional assistance in sample characterization. Two exemplary approaches of introducing a 'treating' flow of, e.g., a compound, a reactant to a given analyte, a salt, and/or a mobile phase, to the captured portion in tube 16 are illustrated in FIGS. 3C-3D and 3E-3F, namely the 'pre-tube' and 'post-tube' approaches.

Figure 3C:
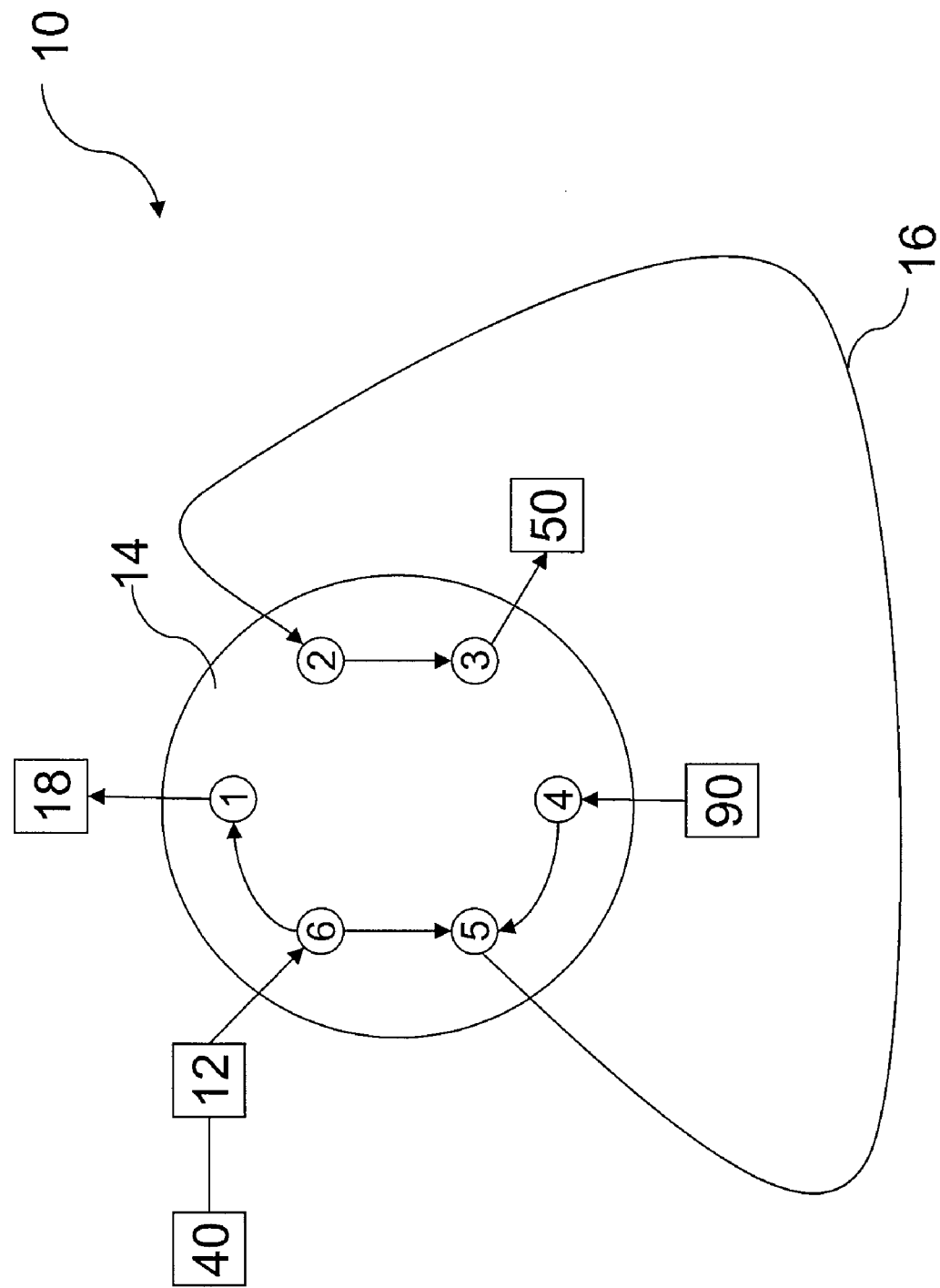
Figure 3D:
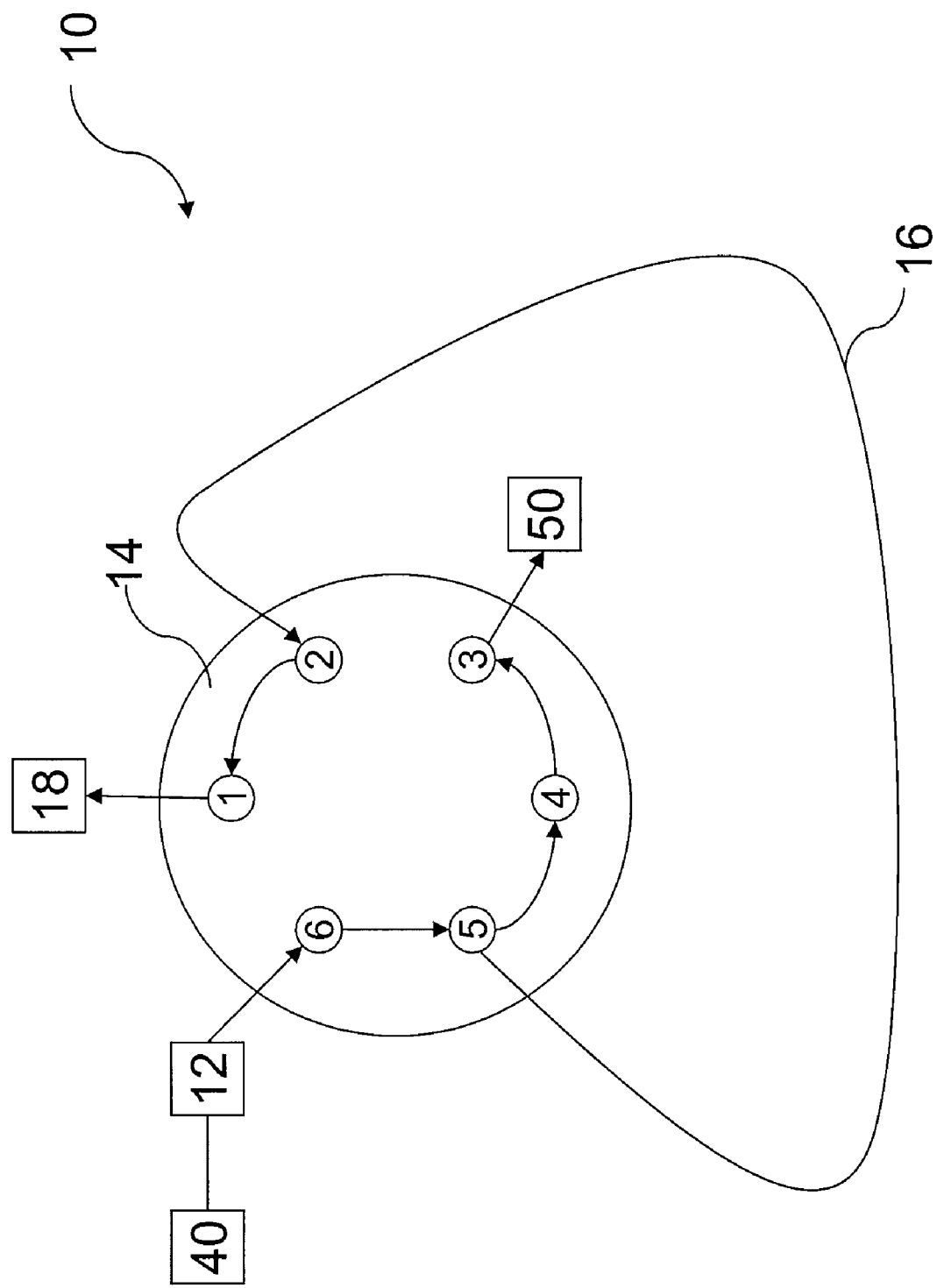

Referring particularly to FIG. 3C, with the 'pre-tube' approach, the 6-port switch valve has an additional groove that connects ports 4 and 5 compared to the valve in its 'splitting and capture' mode as illustrated in FIG. 3A. Port 4 also connects to an ancillary control device 90 to add the 'treating' flow to the captured portion of the LC effluent at the entrance (i.e. port 5) of the tube 16. This approach may be selected when longer treatment time is desired. Device 90 may be a stock solution connected to a pump which can control the flow rate of the solution adding to the captured portion. As discussed above, the split adjuster 50 connected to port 3 can control the split ratio of the LC effluent. Referring to FIG. 3D, the valve is in its 'infusion' mode. The additional groove that connected ports 4 and 5 in FIG. 3C rotates counterclockwise and now connects ports 4 and 3. Similar to the embodiment in FIG. 3B, in the 'infusion' mode, port 3 can optionally connect to split adjuster 50 to control the flow rate of the captured portion entering a mass spectrometer.

Figure 3E:
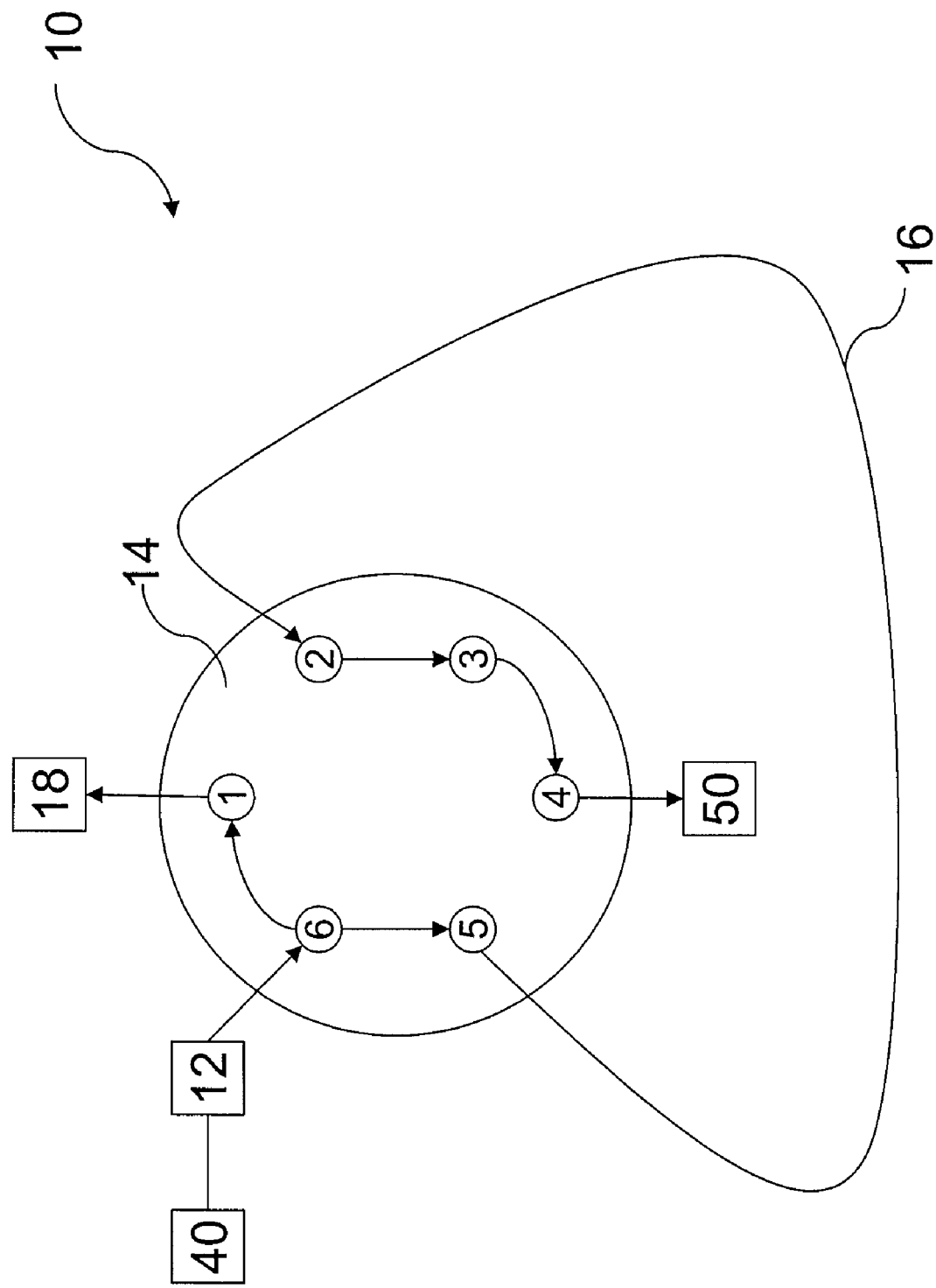
Figure 3F:
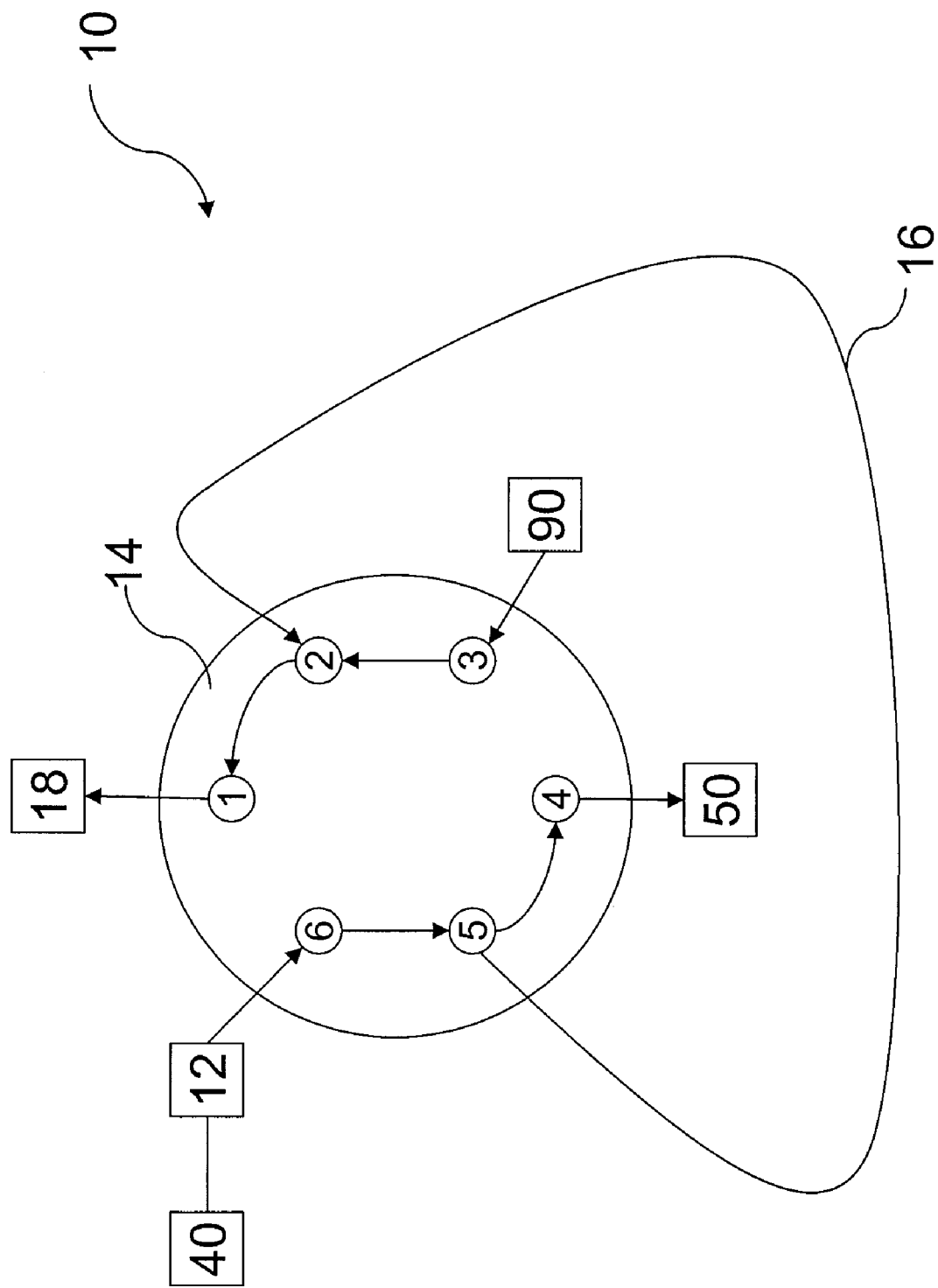

Referring particularly to FIG. 3E, with the 'post-tube' approach, the 6-port switch valve has an additional groove that connects ports 3 and 4 compared to the valve in its 'splitting and capture' mode as illustrated in FIG. 3A. As discussed above, port 4 also optionally connects to a split adjuster 50 to control the split ratio of the LC effluent. Referring to FIG. 3F, the valve is in its 'infusion' mode. The additional groove that connected ports 3 and 4 in FIG. 3E rotates counterclockwise and now connects ports 2 and 3. Port 3 also connects to an ancillary control device 90 to add the 'treating' flow to the captured portion of the LC effluent at the exit (i.e. port 2) of the tube 16. This, approach may be selected when short treatment time is desired. Device 90 may be a stock solution connected to a pump which can control the flow rate of the solution adding to the captured portion. In the 'infusion' mode, port 4 can optionally connect to split adjuster 50 to control the flow rate of the captured portion entering a mass spectrometer.

Figure 3G:
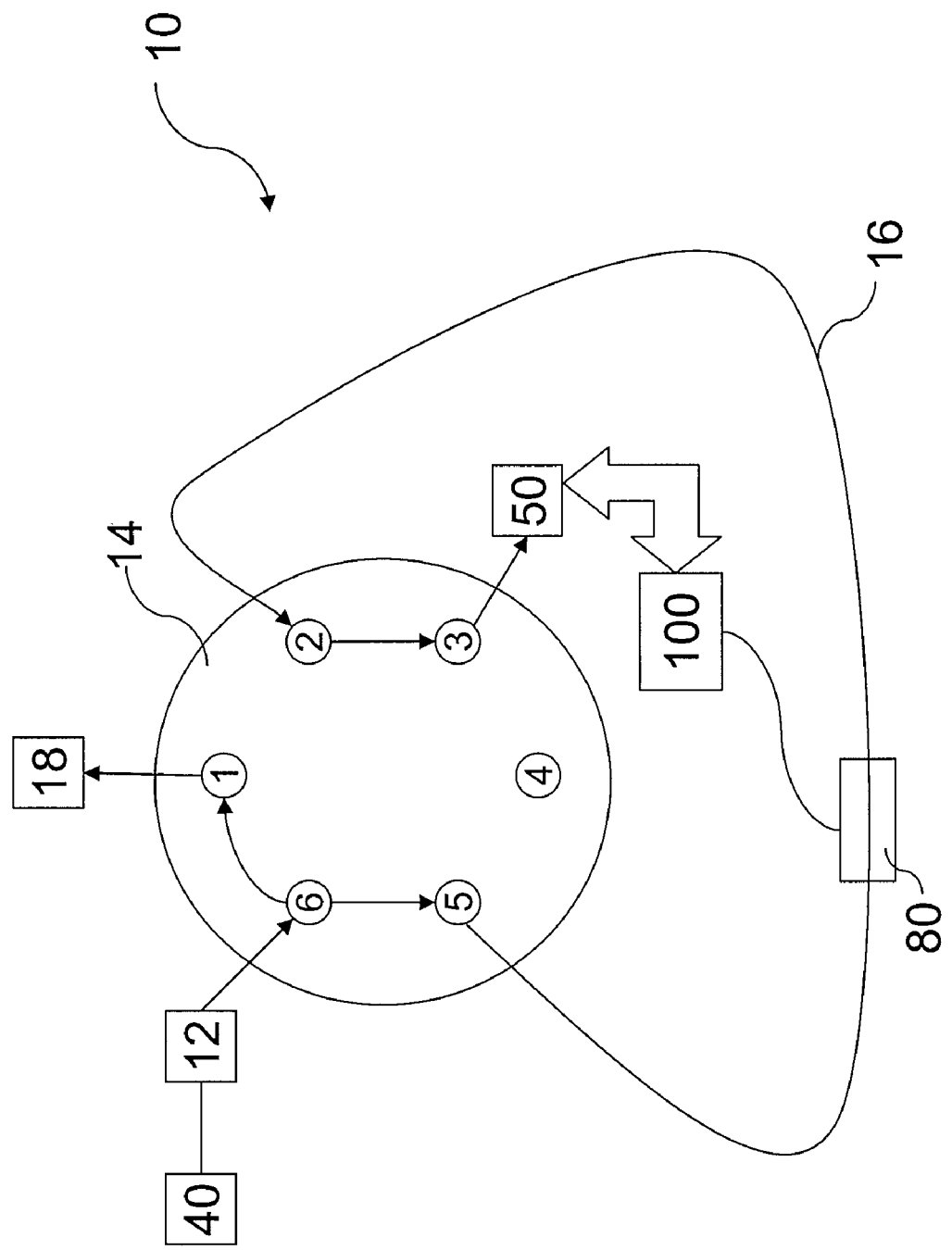

In embodiments, the flow rate can be controlled by a feedback loop including a flow sensor and a split adjuster or a flow controller. As shown is FIG. 3G, a flow rate sensor 80 which is connected to a control unit 100 monitors the flow rate in the tube 16 and sends the information to a split adjuster 50. The split adjuster then adjusts the flow rate accordingly to reach a predetermined value.

In some embodiments, more other features or devices can be included in the LC/MS system 10 to further improve the performance of the system. For example, another LC column (e.g., a nano-LC column) can be placed, e.g., between port 1 and mass spectrometer 18 (e.g., as in FIG. 3G), to further separate and/or concentrate analytes of first portion of the LC effluent of column 12. An additional LC column can also be placed, e.g., at the distal end of tube 16 before the second portion (i.e., the captured portion) of the effluent undergoes MS analysis so that over broadening of chromatographic peaks corresponding to individual analytes due to molecular diffusion in the tube can be counteracted or corrected, for instance.

As discussed above, splitting an LC (e.g., HPLC) effluent prior to a nanoESI analytical device and mass spectrometer enables the acquisition of MS data on all of the components or analytes in the sample, searching the component MS data against a database, then redirecting the portion captured in the capillary tube to the nanoESI/MS device and conducting the MS experiments (e.g., MS/MS) based on the database search results. For example, this disclosure would be useful to analyze a mixture of peptides formed from enzymatically digesting a protein(s) using nanoLC/MS while simultaneously capturing the separated peptides into a tube. At the end of the initial round of nanoLC/MS experiment on the first portion of the sample, the MS data acquired can be analyzed against a database to propose the most probable proteins. Then an intelligent MS experiment targeting peptides that should be present in the second portion of the same sample (i.e., the captured chromatogram in the tube) can be produced to increase the probability of correctly identifying the protein (s), especially if the peptides have very low signal intensities in the initial round of MS. In another example, analysis of intact proteins, which is traditionally difficult for MS to acquire enough data to identify the protein during a single LC/MS experiment, can be achieved with improved accuracy and sensitivity by combining the LC experiment with infusion nanoESI/MS analysis of captured proteins in a tube which substantially remain separated corresponding to the chromatogram. The proteins coming out of the tube may correspond to broader peaks due to diffusion forces, which enables a second, longer MS experiment to be performed on the same injection of a sample. The extended time can allow more signal averaging or multiple MS or MS/MS acquisitions than those using conventional techniques. The diffusion of separated components or analytes in the capture tube can be controlled by various means, such as tube inner diameter, tube length, time in the tube (controlled by length of the nanoLC experiment, for example), or by lowering the tube temperature or introducing barriers between two components to prevent remixing. More discussion follows.

The tube 16 is configured to capture and store a portion of the effluent of the column for a later round of analysis, e.g., with extended analysis time compared to that available for the initial MS scanning of portion 24. In some embodiments, the tube 16 is a capillary tube and its dimension (e.g., inner diameter) is chosen to define a desired range of diffusion of analytes for a desired outcome. For example, the capillary dimensions can be chosen based on the chromatographic peak volume exiting the LC column coupled to the capillary. When using 300 nL/min flow rate from a nano-LC column, peaks that are 12 seconds wide correspond to peak volumes of 60 nL. If a 50 micron inner diameter capillary tube is used as the capture and storing tube, 60 nL corresponds to a length of about 30 mm of the tube. The length of tube can therefore be predetermined to capture and store one or more analyte peaks. In a particular embodiment, the tube can be a fused silica tube with an inner diameter of about 50 µm and a length of around 600 cm. The diameter of the tube is selected to be on the micrometer scale so that diffusion of the captured LC-separated analytes can be controlled, e.g., reducing the likelihood of remixing the separated compounds and losing chromatographic separation.

The techniques described in the present disclosure can take into account characteristics of molecular diffusion in fluids (e.g., eluents) captured in a tube. Molecules (e.g., peptides or proteins) in solution can diffuse randomly in all directions. Molecular diffusion e.g., in a capillary tube, can be predicted based on capillary diameter, size of molecule, bulk solution properties and temperature. The volume of solution where molecules of a given analyte spread per unit length of a capillary is proportional to the square radius of the capillary. In other words, the spreading length of molecules in a solution of fixed volume is inversely proportional to the square radius of the capillary. In addition, the smaller the surface area (e.g. the square radius of the capillary) is, the less frequently or less likely diffusion takes place. As a consequence, reducing or minimizing the change in the volume of a solution of analyte molecules in a tube caused by molecular diffusion and/or reducing the surface area at the boundaries of two analyte zones can be accomplished by use of a capillary with reduced diameter. The effect is to stretch a fixed volume along the length of a capillary. For example, a typical analyte separated by nano-LC at a flow rate of 200 nL/min exits the column in a volume of approximately 50 nL. The length of a 50 nL volume which is dependent on the capillary diameter can vary from about 1 mm to about 2500 mm with capillary diameter changing from 250 µm to 5 µm.

Figure 4:
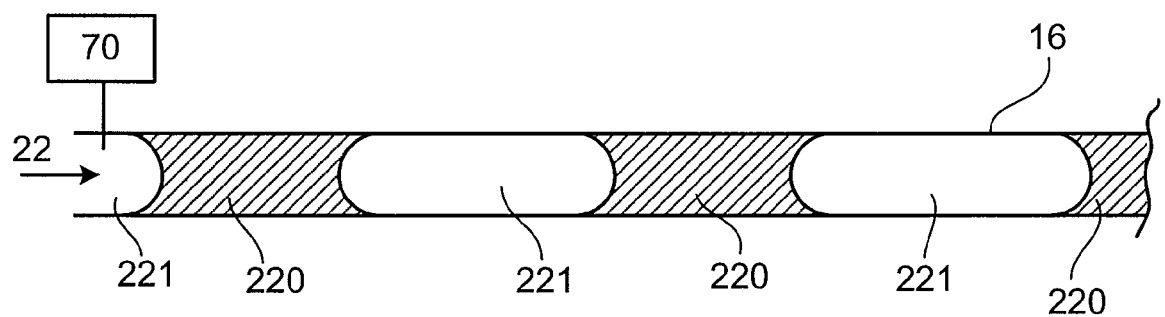
FIG. 4 is a cross-sectional view of an embodiment of a capture tube.

In some embodiments, molecular diffusion in the tube can be controlled for example, by inserting gas bubbles into the capillary to segment the solution, as illustrated in FIG. 4. Molecules in solution can diffuse to the bubble/liquid interface but not beyond it. Referring to FIG. 4, gas segments or bubbles 221 placed between two liquid segments 220 of effluent portion 22 in the capture tube 16. An electrolysis electrode 70 can be placed at the entrance of the tube 16 and programmed to electrolyze the mobile phase to create gas bubbles in a predetermined pattern, for example, gas segments can be created at a defined intervals, e.g., every 50 nL of liquid segment, or gas segments can be created between the elution of two analytes, e.g., right after the elution of a first analyte and before the elution of a second analyte. Further discussion of generating gas segments is disclosed in Khan, et al., "Microfluidic Synthesis of Colloidal Silica", Langmuir, 20, 8604-8611 (2004), and Zheng, et al., "A Microfluidic Approach for Screening Submicroliter Volumes against Multiple Reagents by Using Preformed Arrays of Nanoliter Plugs in a Three-Phase Liquid/Liquid/Gas Flow", Angew. Chem. Int. Ed., 44, 2520-2523 (2005), the entire contents of each of which are hereby incorporated by reference herein. In some embodiments, a reader (optical or thermal) that could detect the bubbles could be used at the exit of tube 16 so that specific liquid segments captured in the tube could be quickly positioned for analysis, e.g., a targeted analysis.

In some embodiments, diffusion can be reduced by cooling the solution to a temperature below the room temperature, e.g., about 4° C. In yet some other embodiments, controlled diffusion (e.g., enhanced diffusion) may be beneficial when the sample is analyzed by infusion nanoESI/MS since the time for acquiring analyte signals and for more MS analyzing cycles will be extended as the analyte diffuses to spread within higher volume which leads to longer time for the analyte to exit the tube at a fixed flow rate. Different embodiments might be combined to achieve the best control of diffusion based on specific requirement of the experiments.

Moreover, other potential benefits of using a tube to store a portion of the LC effluent include keeping the analyte molecules in a solution, e.g., to prevent decomposition of the analyte upon drying or to prevent loss of precious sample by drying and redissolving it in a solvent.

In some embodiments, temperature can be increased. For example, the system can capture intact protein separation, heat and digest proteins with the stored mobile phase.

Mass spectrometer or MS device 18 can be used for tandem MS, e.g., an infusion nanoESI/MS device. The nanoESI sprayer or emitter can be a fused silica capillary with a pulled tip which has an i.d. of about 1-15 µm, or an ESI Chip® available from Advion Biosciences, Inc., which is a microfluidics chip containing an array of nanoelectrospray nozzles, each one-fifth the diameter of a human hair, etched in a silicon wafer for nanoelectrospray.

Many advantages of the techniques described in present disclosure including reserving or storing a portion of a sample have been apparent from the description of different embodiments. One exemplary advantage is that storing a portion of a sample allows subsequent MS experiments to be adjusted to focus on analysis of components or analytes of the sample missed by initial nanoLC/MS experiments. For example, previously identified components of the sample can be excluded from the data dependent acquisition during the subsequent infusion experiment (from the portion stored in the tube), therefore, infusion experiments are able to acquire MS/MS data on the lower-intensity components missed during the initial nanoLC/MS/MS experiment. In some cases, previously identified components of the sample can be included in data dependent acquisition (and others excluded) during the subsequent infusion experiment to further analyze those components in more detail.

A number of embodiments of the invention have been described. Nevertheless, it will be understood that various modifications may be made without departing from the spirit and scope of the invention. For example, the ancillary control device 90 in FIG. 3C can be a pressurized vessel or a pump to introduce gas segments or non-mixing liquid segments into the captured portion to provide diffusion barriers and limit diffusion of analytes. The gas and non-mixing liquid are immiscible with the mobile phase of the LC effluent.

In some embodiments, the split ratio of the LC effluent can be fixed or varied during the division process, e.g., according to the different abundances of analytes, by adjusting the backpressure of the output ports. For example, if analyte A is 10 times as much as analyte B in the sample, when they are separated in the LC column, split ratio of effluent with analyte A may be set to 1:10 while split ratio of effluent with analyte B may be set to 1:1.

In some embodiments, LC effluent directed to the capture capillary could be segmented and fraction collected into individual tubes (e.g., capillaries) with a tapered end on which a nanoESI sprayer could be formed. For example, each of N capillary tube can be connected to a port of a 1:N splitter.

Figure 5A:
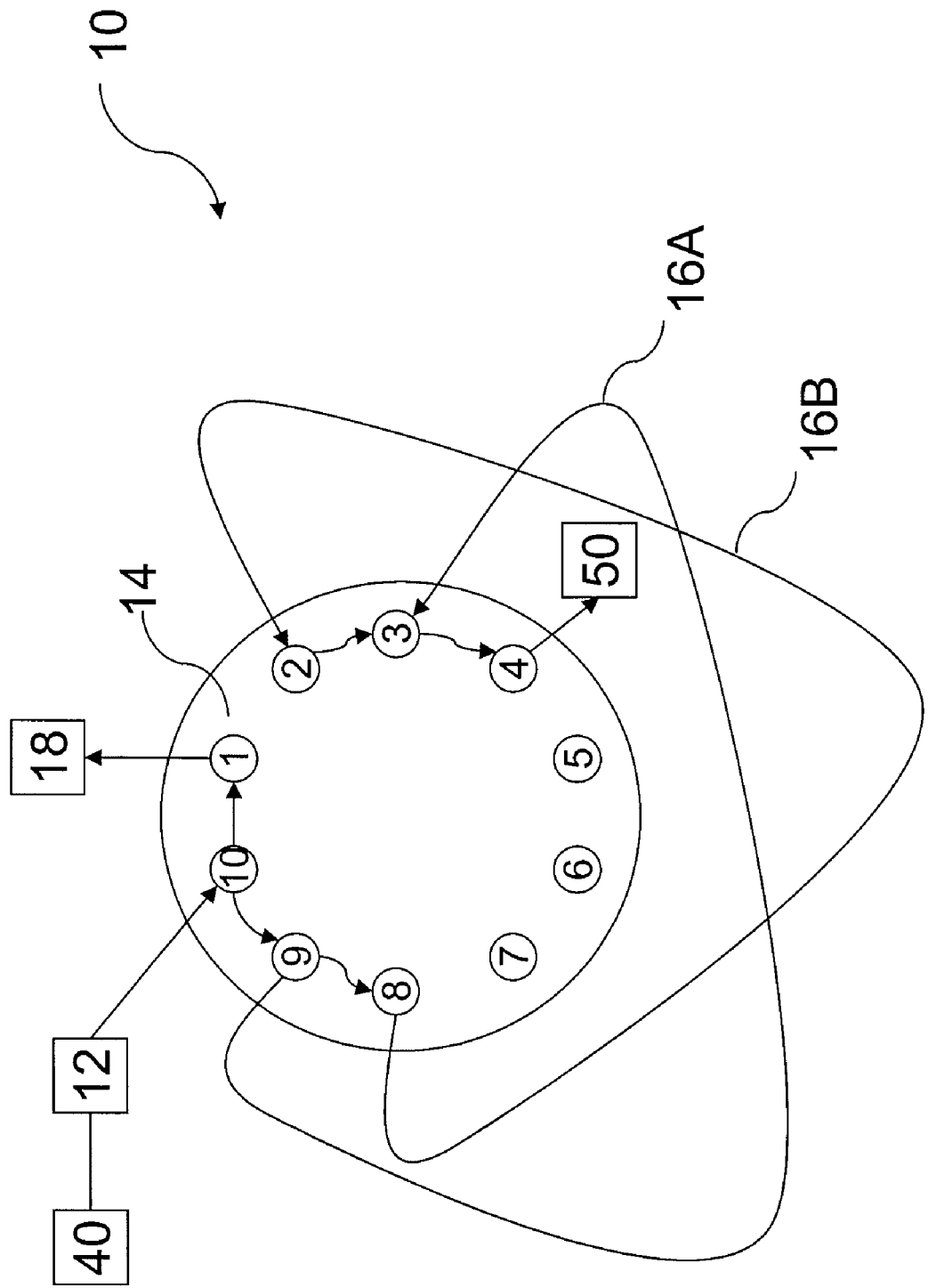
FIGS. 5A and 5B are schematics of still another embodiment.
Figure 5B:
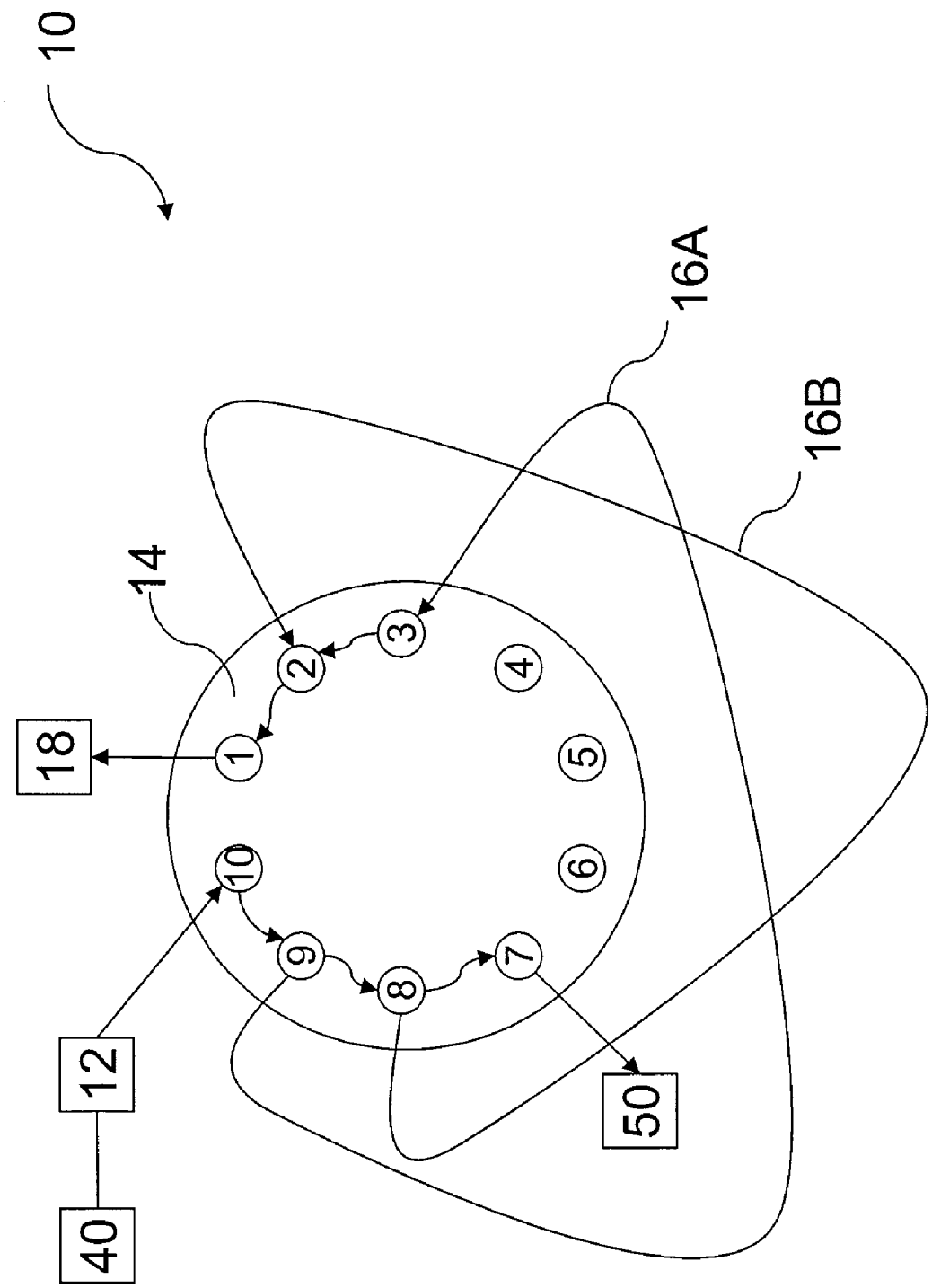
Figure 6A:
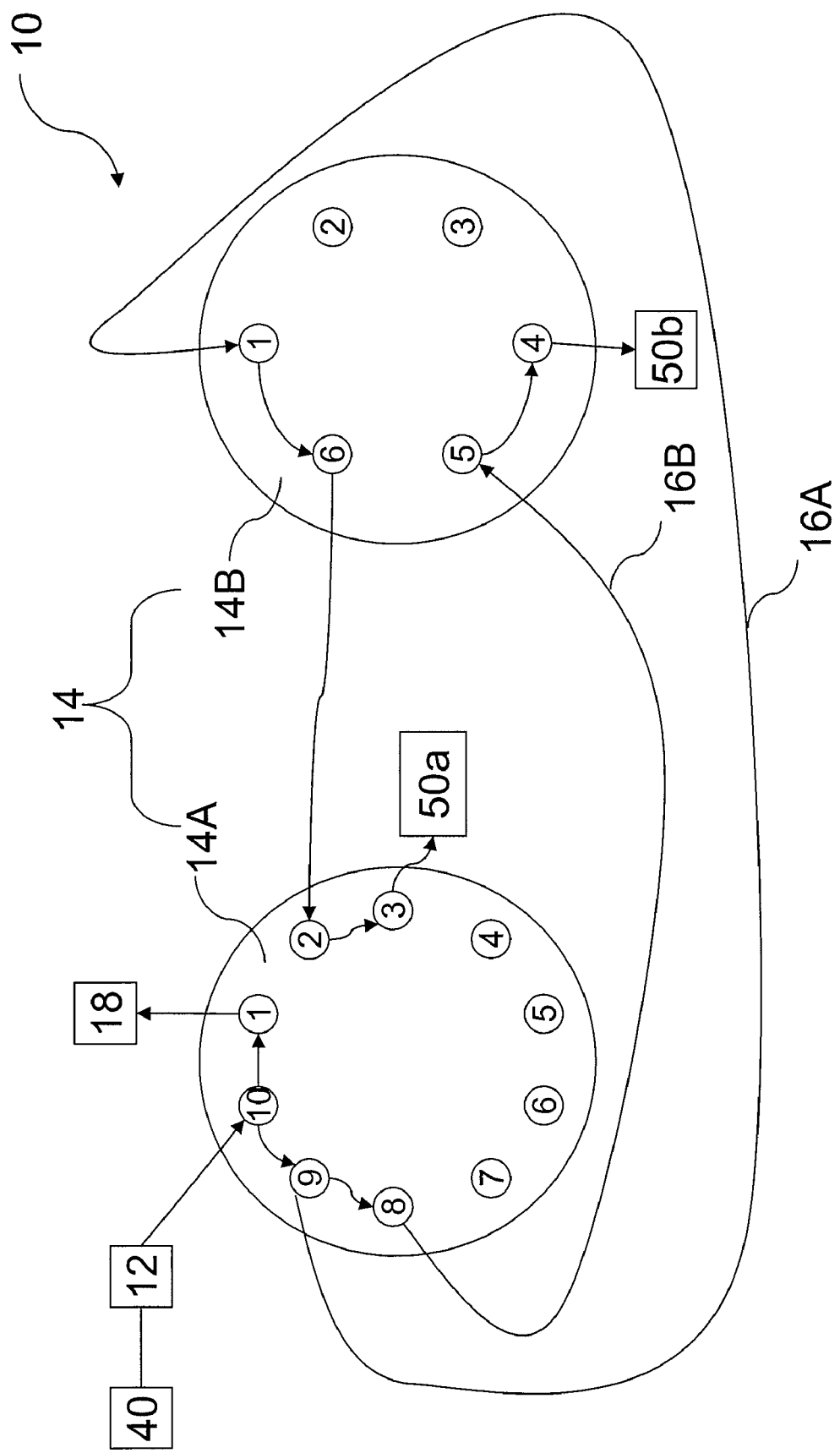
FIGS. 6A-C are schematics of yet another embodiment.
Figure 6B:
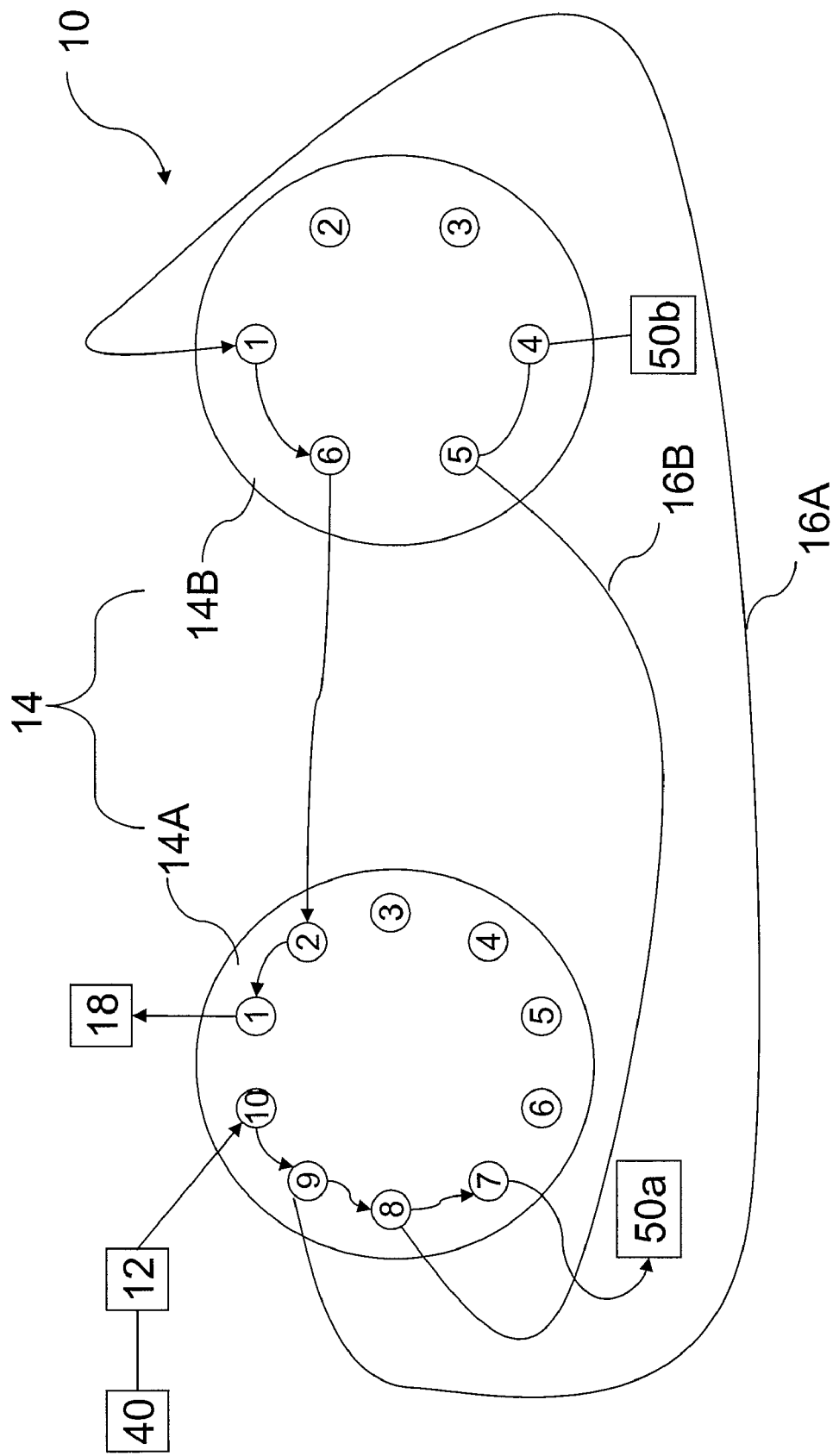
Figure 6C:
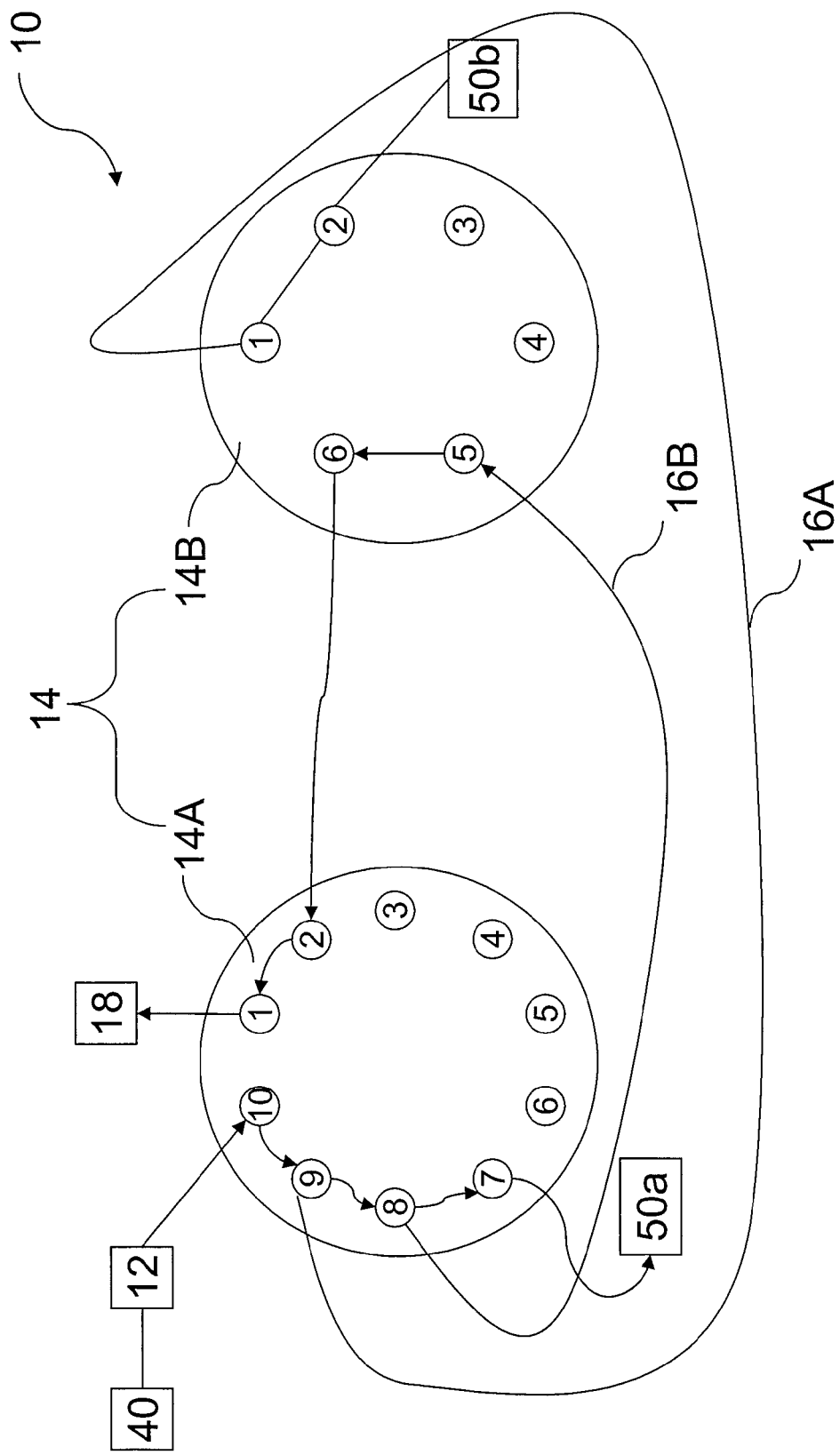

In some embodiments, LC effluent can be divided to more than two portions and at least two portions are captured and stored in individual tubes (e.g., capillaries). For example, as shown in FIGS. 5A and 5B, the splitter 14 can be a ten-port valve. Arrows in these figures indicate flow directions of the analytes. In its 'splitting and capture' mode, as illustrated in FIG. 5A, the valve first splits the LC effluent from column 12 to two flows at port 10 with a first flow to port 1 then the mass spectrometer 18 and a second flow to port 9 which splits the flow again so that one portion of the second flow is captured in tube 16A while the other portion of the second flow is directed to port 8 and captured in tube 16B. The split adjuster 50 controls the split ratio of the first and second flow. In the 'infusion' mode, as illustrated in FIG. 5B, the captured portions in tubes 16A and 16B are driven to pass out of the tubes for analysis by the mobile phase of the column 12 connected to the pump 40. Or in another example, the splitter 14 can be a valve assembly that includes a ten-port valve 14A and a six-port valve 14B connected by two capture tubes 16A and 16B, as illustrated in FIGS. 6A-6C. Arrows in these figures indicate flow directions of the analytes. Compared to a single multi-port valve, this valve assembly configuration enables individual controls over the flow rates of the individual captured portions thus enables control over both the split ratio of the initial LC effluent and the split ratio of the primary captured portion that is further split into at least two subsidiary captured portions. Referring particularly to FIG. 6A, as in the 'splitting and capture' mode, the ten-port valve 14A first splits the LC effluent from column 12 to two flows at port 10 with a first flow to port 1 then the mass spectrometer 18 and a second flow to port 9 which splits the flow again so that one portion of the second flow is captured in tube 16A while the other portion of the second flow is directed to port 8 and captured in tube 16B. Two split adjusters 50a and 50b that are in fluid communication with individual captured portions control the backpressures thus the flow rates in the capture tubes. The flow rate ratio of captured portions in tube 16A and 16B can be selected by controlling split adjusters 50a and 50b with respect to each other while the split ratio of the LC effluent (split to first and second flows) can be adjusted by controlling either or both of two split adjusters. Referring to FIGS. 6B and 6C, as in the 'infusion' mode, either the captured portion in tube 16A or the portion in tube 16B may be redirected to a mass spectrometer for analysis while the other captured portion can be kept in the tube for later analysis.

Figure 7A:
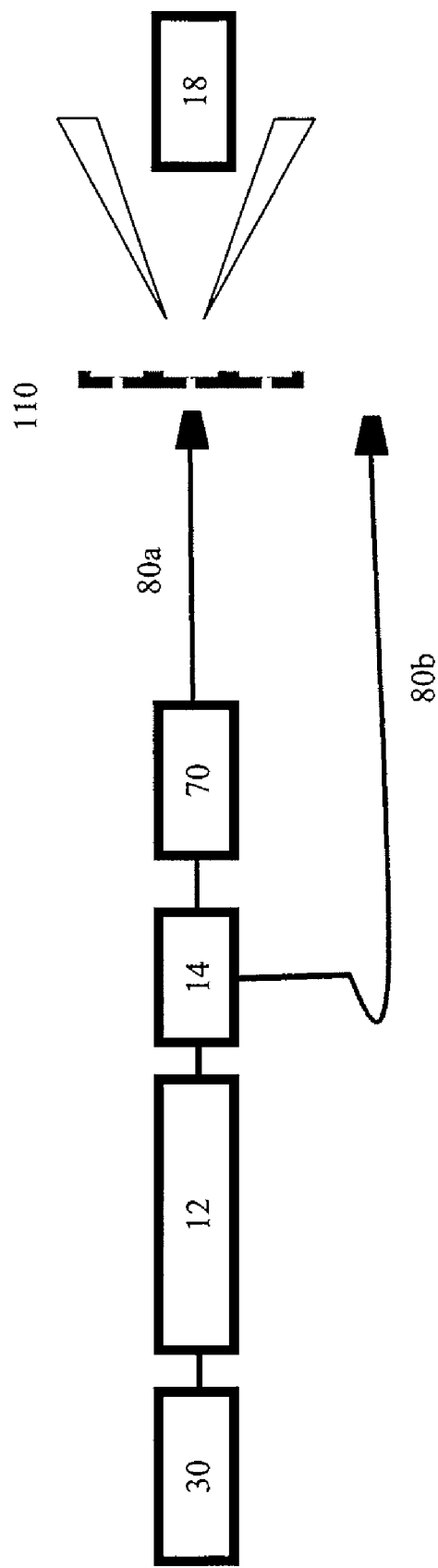

In some embodiments, one portion of the effluent of a nanoLC column is driven to the mass spectrometer while another portion is captured by a capillary tube. Referring to FIG. 7A, the effluent passes from the autosampler 30 into the LC column 12 and into the splitter 14. A first portion of the effluent passes into a second, smaller ID column 70 and then passes through a coupling device 80a that connects to a nanospray chip 110 with multiple channels. A second portion of the effluent progresses from the splitter 14 through a capture capillary 80b. The capture capillary 80b consists of a long capillary with a second chip coupling device at its end, which can be coupled to the chip 110 (but is not coupled in FIG. 7A). After the nanoLC run has ended, the capture capillary 80b couples to the channel of the micro chip 110 through the coupling mechanism.

The effluent can be directed into column 70 or into capillary tube 80b by controlling the back pressures of the output ports of the splitter. Factors that influence back pressure include the inner diameters and the lengths of the output ports as well as the tubes connected to them. In some embodiments, the inner diameters of the output ports and/or the tubes connected to them can be about 5 microns to 750 microns, e.g., 10 to 500 microns, 20 to 200 microns, or 50 to 100 microns. For example, in a particular embodiment, the port leading to column 70 can have an i.d. of 15 microns and 15 centimeters of total tubing length while the capillary 80b can have an i.d. of 50 microns and 15 centimeters of total tube length to achieve a flow rate ratio of 1:3. Back pressure can also be affected by applying an external pressure to the split portions via, e.g., a spit adjustor.

Referring to FIG. 7B, in some embodiments, the second portion passes from splitter 14 through capillary 80c and into the 6 port valve 60, where it flows through two connected channels (e.g., channels 1 and 6) into the capillary 80b. The flow of the second portion can be controlled by using a pressure bomb 120 that is connected, e.g., to channel 5. The pressure bomb 120 is a chamber that can be equipped with a small gas cylinder, a high pressure gauge, and a thick-walled metal chamber. The pressure bomb can drive the captured portion of LC effluent to the MS device 18. The flow rate can also depend on the tubing i.d. and length.

Referring to FIG. 7C, after the nanoLC run has ended, the valve 60 switches to a second mode that connects the two ports with the pressure bomb 120 and the capture capillary. At the same time, the capture capillary 80b couples to the channel of the micro chip 110 through the coupling mechanism.

A person of skill in the art will appreciate that the additional techniques of temperature control and diffusion control, described earlier in the application, can be combined with the embodiments involving an effluent that is separated into multiple portions.

All publications, patent applications, patents, and other references mentioned herein including the appendix, are incorporated by reference herein in their entirety.

Still other embodiments are within the following claims.

What is claimed is:

1. A liquid chromatography system, comprising:
   a chromatographic column through which an effluent passes, wherein the effluent comprises a plurality of analytes that correspond to a plurality of chromatographic peaks and an eluent;
   a post-column splitter having at least two output ports through which the effluent of the column is split to at least a first portion and a second portion;
   a mass spectrometer configured to receive the first portion from a first of the output ports for analysis; and
   a tube connected to a second of the output ports configured to prevent substantial evaporation of the eluent in the second portion, having a plurality of separated analytes corresponding to at least two chromatographic peaks, until undergoing mass spectrometry.

2. The system of claim 1, configured to direct the second portion to the mass spectrometer after the first portion is analyzed by the mass spectrometer.

3. The system of claim 1, further comprising a pump connected to the tube to pump the second portion to the mass spectrometer after the first portion is analyzed by the mass spectrometer.

4. The system of claim 1, further comprising a second detector configured to receive the second portion from the tube after the first portion is analyzed by the mass spectrometer.

5. The system of claim 4, wherein the second detector comprises a mass spectrometer.

6. The system of claim 4, wherein the second detector comprises an infusion nanoESI/MS device.

7. The system of claim 1, wherein the tube is configured to substantially reduce the diffusion of the analytes in the effluent stored in the tube.

8. The system of claim 1, wherein the tube is configured to stay at a temperature lower than the room temperature.

9. The system of claim 1, wherein the tube comprises an electrolysis electrode to electrolyze the eluent to produce a gas segment between any two eluent segments.

10. The system of claim 9, wherein the electrolysis is triggered by an analytical device.

11. The system of claim 10, wherein the device is an ultraviolet detector, fluorescence detector, an electrochemical detector, evaporative light scattering detector, nuclear magnetic resonant spectrometer, charged aerosol detector, refractive index detector, or a mass spectrometer.

12. The system of claim 1, wherein the mass spectrometer comprises an electrospray sprayer.

13. The system of claim 1, wherein the mass spectrometer comprises an ESI/MS device.

14. The system of claim 1, wherein the mass spectrometer comprises an infusion nanoESI/MS device.

15. The system of claim 14, wherein the infusion nanoESI/MS device comprises a nanoESI sprayer.

16. The system of claim 15, wherein the nanoESI sprayer comprises a pulled tip of a fused silica capillary.

17. The system of claim 14, wherein the infusion nanoESI/MS device comprises a chip containing an array of nanoelectrospray nozzles.

18. The system of claim 1, wherein the tube comprises a fused silica capillary.

19. The system of claim 1, wherein the tube has a diameter of 250 μm or less.

20. The system of claim 1, wherein the tube has a diameter of 100 μm or less.

21. The system of claim 1, wherein the tube has a diameter of 75 μm or less.

22. The system of claim 1, wherein the tube has a diameter of 50 μm or less.

23. The system of claim 1, wherein the tube has a length of about 1 meter or more.

24. The system of claim 1, wherein the tube has a length of about 10 meters or less.

25. The system of claim 1, wherein the tube has a length of about 6 meters.

26. The system of claim 1, wherein the second portion is directed for mass spectrometry at a lower flow rate than the first portion is.

27. The system of claim 1, wherein the splitter comprises a T-shape piece that creates a volume ratio of about 4:1 to about 1:1 of the second portion to the first portion.

28. The system of claim 1, wherein the splitter comprises a valve that has at least five ports, a first connector connecting two of said ports, and a second connector connecting three or more of the rest said ports to split the effluent.

29. The system of claim 28, wherein the valve has at least six ports.

30. The system of claim 28, wherein the valve has at least one port connected to a flow controller.

31. The system of claim 28, wherein the valve has two ports that are connected by the tube.

32. The system of claim 28, wherein the valve is switchable between at least two configurations, including a first configuration in which the second connector connects a first set of three ports, and a second configuration in which the second connector connects a second set of ports different from the first set.

33. The system of claim 1, wherein the analytes in the second portion exit the tube in the same order in which the analytes exit the chromatographic column.

34. The system of claim 1, wherein the analytes in the second portion exit the tube in a reversed order in which the analytes exit the chromatographic column.

35. The system of claim 1, wherein the second portion is mixed with a stream of liquid before the portion undergoes mass spectrometry.

36. The system of claim 1, wherein the second portion has a plurality of separated analytes corresponding to at least half of the plurality of chromatographic peaks corresponding to the analytes that pass through the chromatographic column.

37. The system of claim 36, wherein the second portion has a plurality of separated analytes corresponding to at least 90% of the plurality of chromatographic peaks corresponding to the analytes that pass through the chromatographic column.

38. The system of claim 1, further comprising a second chromatographic column, wherein the inner diameter of the second column is smaller than that of the first column.

39. The system of claim 28, further comprising a second chromatographic column, wherein the inner diameter of the second column is smaller than that of the first column.

40. A method of characterizing an analyte in a sample, the method comprising:
passing an effluent comprising a plurality of analytes and an eluent through a chromatographic column, the analytes corresponding to a plurality of chromatographic peaks;
splitting at least a first portion and a second portion of the effluent from respective output ports of a post-column splitter, the first portion being directed from a first of the output ports to a mass spectrometer for analysis; and
receiving the second portion having a plurality of separated analytes corresponding to at least two chromatographic peaks in a tube connected to a second of the output ports to prevent substantial evaporation of the eluent before undergoing mass spectrometry.

41. The method of claim 40, further comprising directing the second portion from the tube to the mass spectrometer after the first portion is analyzed by the mass spectrometer.

42. The method of claim 40, further comprising directing the second portion from the tube to a second mass spectrometer after the first portion is analyzed by the mass spectrometer.

43. The method of claim 40, further comprising analyzing a first analyte from the stored second portion after a second analyte from the first portion has been analyzed by the mass spectrometer, wherein the first analyte passed out of the chromatographic column before the second analyte passed out of the chromatographic column.

44. The method of claim 40, further comprising analyzing a first analyte from the stored second portion after a second analyte from the second stored portion has been analyzed by the mass spectrometer, wherein the first analyte passed out of the chromatographic column before the second analyte passed out of the chromatographic column.

45. The method of claim 40, further comprising analyzing a first analyte from the stored second portion before a second analyte from the second stored portion has been analyzed by the mass spectrometer, wherein the first analyte passed out of the chromatographic column before the second analyte passed out of the chromatographic column.

46. The method of claim 40, further comprising cooling the second portion to substantially reduce diffusion of the analytes in the eluent captured in the tube.

47. The method of claim 40, further comprising segmenting the stored second portion into a least two segments in the tube by a gas bubble wherein the gas bubble creates a diffusion boundary to the analytes in the portion.

48. The method of claim 47, wherein the gas bubble is formed by electrolysis of the eluent of the second portion.

49. The method of claim 47, further comprising recording the segment positions in the tube by counting gas bubbles.

50. The method of claim 40, further comprising segmenting the stored second portion into a least two segments in the tube by a non-mixing liquid segment wherein the non-mixing liquid segment creates a diffusion boundary to the analytes in the portion.

51. The method of claim 40, further comprising directing the stored second portion in the tube to the mass spectrometer at a calibrated flow rate controlled by a pump connected to the tube.

52. The method of claim 51, wherein the calibrated flow rate less is than 5,000 nL/min.

53. The method of claim 51, wherein the calibrated flow rate less is than 1,000 nL/min.

54. The method of claim 51, wherein the calibrated flow rate less is than 2 nL/min.

55. The method of claim 40, wherein the second portion has a plurality of separated analytes corresponding to at least half of the plurality of chromatographic peaks corresponding to the analytes that pass through the chromatographic column.

56. The method of claim 55, wherein the second portion has a plurality of separated analytes corresponding to at least 90% of the plurality of chromatographic peaks corresponding to the analytes that pass through the chromatographic column.

57. The method of claim 40, further comprising directing the effluent into a second chromatographic column.

58. The method of claim 57, wherein the directing is performed by controlling back pressures of the splitter by connecting a pump to a port of the splitter.

* * * * *

UNITED STATES PATENT AND TRADEMARK OFFICE
CERTIFICATE OF CORRECTION

PATENT NO. : 7,797,988 B2
APPLICATION NO. : 12/053051
DATED : September 21, 2010
INVENTOR(S) : Gary A. Schultz, Reinaldo Rodrigo Queiros de Almeida and Mark Haydn Allen It is certified that error appears in the above-identified patent and that said Letters Patent is hereby corrected as shown below:

Claim 47, Column 19, Line 2 – delete "a least" and insert -- at least --, therefore.

Claim 50, Column 19, Line 11 – delete "a least" and insert -- at least --, therefore.

Claim 52, Column 19, Line 20 – delete "less is than" and insert -- is less than --, therefore.

Claim 53, Column 20, Line 2 – delete "less is than" and insert -- is less than --, therefore.

Claim 54, Column 20, Line 4 – delete "less is than" and insert -- is less than --, therefore.

Signed and Sealed this
Twenty-fifth Day of January, 2011

David J. Kappos
*Director of the United States Patent and Trademark Office*